US012808002B2

(12) United States Patent
Hudson et al.

(10) Patent No.: US 12,808,002 B2
(45) **Date of Patent: *Nov. 24, 2026**

(54) **PROBES FOR DETECTING *CANDIDA GLABRATA***

(71) Applicant: Gen-Probe Incorporated, San Diego, CA (US)

(72) Inventors: Angela S. Hudson, San Diego, CA (US); Damon K. Getman, Poway, CA (US); Alice Jiang, San Diego, CA (US); Barbara Eaton, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 190 days.

This patent is subject to a terminal disclaimer.

(21) Appl. No.: 18/295,924

(22) Filed: Apr. 5, 2023

(65) Prior Publication Data

US 2023/0295745 A1 Sep. 21, 2023

Related U.S. Application Data

(60) Division of application No. 17/371,274, filed on Jul. 9, 2021, now Pat. No. 12,467,101, which is a continuation of application No. 16/065,461, filed as application No. PCT/US2017/012163 on Jan. 4, 2017, now Pat. No. 11,111,549.

(60) Provisional application No. 62/274,610, filed on Jan. 4, 2016.

(51) Int. Cl.
*C12Q 1/6895* (2018.01)
*C12Q 1/6806* (2018.01)
*C12Q 1/686* (2018.01)
*C12Q 1/689* (2018.01)

(52) U.S. Cl.
CPC ......... *C12Q 1/6895* (2013.01); *C12Q 1/6806* (2013.01); *C12Q 1/686* (2013.01); *C12Q 1/689* (2013.01); *C12Q 2600/112* (2013.01); *C12Q 2600/16* (2013.01); *C12Q 2600/166* (2013.01)

(58) Field of Classification Search
CPC .... C12Q 1/6895; C12Q 1/6806; C12Q 1/686; C12Q 1/689; C12Q 2600/112; C12Q 2600/16; C12Q 2600/166
See application file for complete search history.

(56) References Cited

U.S. PATENT DOCUMENTS

| | | | |
|---|---|---|---|
| 6,235,890 B1 | 5/2001 | Morrison et al. | |
| 6,534,274 B2 | 3/2003 | Becker et al. | |
| 6,849,412 B2 | 2/2005 | Becker et al. | |
| 2004/0023207 A1 | 2/2004 | Polansky | |
| 2008/0268452 A1 | 10/2008 | Kaplan | |
| 2009/0170110 A1* | 7/2009 | Hogan | C12Q 1/6895 435/6.15 |
| 2013/0280708 A1 | 10/2013 | Neely et al. | |
| 2014/0018445 A1 | 1/2014 | Hermann et al. | |

FOREIGN PATENT DOCUMENTS

| | | |
|---|---|---|
| CN | 104232745 A | 12/2014 |
| CN | 104884638 A | 9/2015 |
| JP | 2008513009 A | 5/2008 |
| WO | 2006031870 A2 | 3/2006 |
| WO | 2009085704 A2 | 7/2009 |
| WO | 2013158281 A1 | 10/2013 |
| WO | 2014059260 A2 | 4/2014 |
| WO | 2015023892 A1 | 2/2015 |
| WO | 2016172204 A1 | 10/2016 |

OTHER PUBLICATIONS

Innings (Journal of Clinical Microbiology, Mar. 2007, p. 874-880).*
Hua (PLOS Biology (2007 vol. 5, e73, pp. 0729-0744).*
Udenfriend (Analytical Biochemistry (1962) vol. 3, p. 49-61.*
Kachouri (RNA (2005), 11:1064-1072).*
Non-Final Office Action mailed Nov. 26, 2024, issued in corresponding U.S. Appl. No. 18/295,351, filed Apr. 4, 2023, 37 pages.
Dieffenbach et al.; "Genome Research—General concepts for PCR primer design"; PCR Methods Appl.; 1993; pp. 30-37; vol. 3; Cold Spring Harbor Laboratory Press.
Innings et al.; "Multiplex Real-Time PCR Targeting the RNase P RNA Gene for Detection and Identification of *Candida* Species in Blood"; Journal of Clinical Microbiology; Mar. 2007; pp. 874-880; vol. 45; No. 3; American Society for Microbiology.
Zangenberg, G., et al., "Multiplex PCR: Optimization Guidelines," PCR Applications, Chapter 6, pp. 73-94, Academic Press, 1999.
International Search Report and Written Opinion of the International Searching Authority mailed Jul. 21, 2017, issued in corresponding International Application No. PCT/US2017/012163, filed Jan. 4, 2017, 25 pages.
Non-final Office Action dated Apr. 23, 2025, issued in corresponding U.S. Appl. No. 17/371,274, filed Jul. 9, 2021 (29 pages).
Examination Report dated Oct. 21, 2024, issued in corresponding Australian Application No. 2023202340, filed Apr. 17, 2023 (4 pages).
Examination Report dated Dec. 20, 2024, issued in corresponding Australian Application No. 2023202333, filed Apr. 17, 2023 (3 pages).
Examination Report dated Mar. 10, 2021, issued in corresponding European Application No. 17704329.6, filed Jan. 4, 2017 (5 pages).
Examination Report dated Nov. 21, 2023, issued in corresponding European Application No. 23169555.2, filed Jan. 4, 2017 (10 pages).

(Continued)

*Primary Examiner* — Steven Pohnert
(74) *Attorney, Agent, or Firm* — Sherbina Intellectual Property Law, PLLC; Nicholas V. Sherbina; Jeffrey E. Landes

(57) ABSTRACT

Disclosed are methods utilizing specific amplification of *Candida* sp. target nucleic acid for detecting the presence or absence of *Candida* sp. in a sample. Also disclosed are corresponding oligomers, including amplification oligomers, capture probes and detection probes, and combinations thereof, as well as corresponding reaction mixtures and kits.

18 Claims, 3 Drawing Sheets

Specification includes a Sequence Listing.

(56) References Cited

OTHER PUBLICATIONS

Examination Report dated Nov. 21, 2023, issued in corresponding European Application No. 23169947.1, filed Jan. 4, 2017 (11 pages).

Examiner's Requisition mailed Jun. 23, 2025, issued in corresponding Canadian Application No. 3,010,232, filed Jan. 4, 2017 (10 pages).

Final Office Action dated Jun. 27, 2025, issued in corresponding U.S. Appl. No. 18/295,351, filed Apr. 4, 2023 (14 pages).

Nour-Eldin, H.H., et al., "User Cloning and User Fusion: The Ideal Cloning Techniques for Small and Big Laboratories," A.G. Fett-Neto (ed.), Plant Secondary Metabolism Engineering, Methods in Molecular Biology 643, 2010.

Jorgensen, M.E., et al., "Design and Direct Assembly of Synthesized Uracil-containing Non-clonal DNA Fragments into Vectors by User Cloning," Bio Protoc 7:e2615, Nov. 20, 2017, DOI: 10.21769/BioProtoc2615.

* cited by examiner

```
ccggtcaaca taaggagttt tctttagaaa ctcattcaca accaaatgcg ggtgggaaat
tcggtggtac gctccatcct ttacagattt gctcctgaga gcttcttcct tagcgtgaaa
gcgcatgggc ggcgttacaa gaaatataca cggagtttta aggctgtaga aggtctgctt
cgtatgggaa tggcgccgtg gatggttggc tgtgagtaat tctttactac aagctgttta
gtgcaatatg cgaacttgaa gtcaccttca agcacccgat accgatcacc gacttgagac
aggtttta
```

FIG. 1 ggattacagc ttagtggagc ttggagtata ggtgctcctc tgagttcatt ttgagcctct
gggtactctt gagagtactg actcttacgc ggttggttac atgtggtttg aaggtctttt
ctgagggttt ttctgttgga ggttacggga gttgtgtgtg tcggtgtatt gtcgtggagc
ttcacttgga gttgtctgcg tctcagagca agtcgtgggg attatgtctt ttggctgtcc
gttcgttttc ctcttcacct ttctgcttgt acaataggtc ttgtagagct ccagtgctat
tcttagtcga ccgtgaggac ggctttcggg ggaacccggc cggtaagatt aagtgcattg
gagtttctgc tgaaatctgt atcgtataag gaggataagg gtggggcaga gacgtatggg
cctgtctagg gatgtgactg tcatgcgctt ttctgagaag caacttctct attaacggtg
gatttgtgcg acacttctcc attgctcact tcctctctaa tggagggccc tacgtaagga
tgtcggtcca gtatgtctgc gattgtttct gtggtggacc tcgcgctgtt ataagaaata
tacccgtttc gcttctggtt ttctgagcag gaagatatat ttccagtgaa gatgcaccag
gagcaacggc tgggaatggc agcggattaa gaaagccact gaaaactctc gcaggtgcat
tgggtagaga aagcctgcgt attttctttc cacatattcc tacatcacta tgaagggtgg
agctttcctc tcttcagaga tgttccgtag ttctctgggg tgcttagttt gatcatgtgg
tgcgtcttct tcttagtttc acggcttggc tcacacactt tgtcgcttta aacctgccat
ttccgctctc ttaagagagt gcattggtgt gaggcgaggt gtcaaaatcg tggtgaggct
ttattcagtg caattgtagg acttgtcgtc tcgttagaga tgatttga

FIG. 2

```
gagctcgact cgtctcgatt cgcattgacc cgcgaacaaa aggaactttc cgttcaaaag
caaaaattat gcgggtggga aattcggtgg tactctccat tcattcaaga tttgtgctcc
tgagagcaaa ttcctgagcg tgcaaacgca tgggcggtgt taaaagaaat cttcagagcc
cgaaggcgcc cgactacctt cggtagtttg gcttttcttt gggttctatg ggaatgacgc
cgtgaatggt tggctgttgt ttagtgtcaa agcgaacaag ggctatttag tgcaatatgc
gaacttgatg gttgttcata actgtcaaga acccgatacc gatcattgac gatgagttga
gttaa
```

FIG. 3

SEQUENCE LISTING

```
Sequence total quantity: 155
SEQ ID NO: 1           moltype =   length =
SEQUENCE: 1
000

SEQ ID NO: 2           moltype =   length =
SEQUENCE: 2
000

SEQ ID NO: 3           moltype = RNA  length = 25
FEATURE                Location/Qualifiers
source                 1..25
                       mol_type = other RNA
                       organism = synthetic construct
misc_feature           1..25
                       note = Synthetic Oligonucleotide
SEQUENCE: 3
ccaagtcctt gtggcttggc cttgg                                        25

SEQ ID NO: 4           moltype = DNA  length = 28
FEATURE                Location/Qualifiers
misc_feature           1..28
                       note = Synthetic Oligomer
source                 1..28
                       mol_type = other DNA
                       organism = synthetic construct
SEQUENCE: 4
atgggaatgg cgccgtggat ggtcccat                                     28

SEQ ID NO: 5           moltype =   length =
SEQUENCE: 5
000

SEQ ID NO: 6           moltype = DNA  length = 18
FEATURE                Location/Qualifiers
misc_feature           1..18
                       note = Synthetic Oligomer
source                 1..18
                       mol_type = other DNA
                       organism = synthetic construct
SEQUENCE: 6
gtgggaaatt cggtggta                                                18

SEQ ID NO: 7           moltype = DNA  length = 22
FEATURE                Location/Qualifiers
misc_feature           1..22
                       note = Synthetic Oligomer
```

```
source                  1..22
                        mol_type = other DNA
                        organism = synthetic construct
SEQUENCE: 7
gaaattcggt ggtacgctcc at                                           22

SEQ ID NO: 8            moltype =   length =
SEQUENCE: 8
000

SEQ ID NO: 9            moltype = DNA  length = 46
FEATURE                 Location/Qualifiers
misc_feature            1..46
                        note = Synthetic Oligonucleotide
regulatory              1..27
                        regulatory_class = promoter
source                  1..46
                        mol_type = other DNA
                        organism = synthetic construct
SEQUENCE: 9
aatttaatac gactcactat agggagatca agttcgcata ttgcac                 46

SEQ ID NO: 10           moltype = DNA  length = 47
FEATURE                 Location/Qualifiers
misc_feature            1..47
                        note = Synthetic oligomer
regulatory              1..27
                        regulatory_class = promoter
source                  1..47
                        mol_type = other DNA
                        organism = synthetic construct
SEQUENCE: 10
aatttaatac gactcactat agggagatga tcggtatcgg gtgcttg                47

SEQ ID NO: 11           moltype = DNA  length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 11
agtgcattgg agtttctgc                                               19

SEQ ID NO: 12           moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 12
gcattggagt ttctgctg                                                18

SEQ ID NO: 13           moltype = DNA  length = 45
FEATURE                 Location/Qualifiers
misc_feature            1..45
                        note = Synthetic Oligonucleotide
regulatory              1..27
                        regulatory_class = promoter
source                  1..45
                        mol_type = other DNA
                        organism = synthetic construct
SEQUENCE: 13
aatttaatac gactcactat agggagaacc gacatcctta cgtag                  45

SEQ ID NO: 14           moltype = DNA  length = 49
FEATURE                 Location/Qualifiers
misc_feature            1..49
                        note = Synthetic Oligonucleotide
regulatory              1..27
                        regulatory_class = promoter
source                  1..49
                        mol_type = other DNA
                        organism = synthetic construct
SEQUENCE: 14
aatttaatac gactcactat agggagaata ctggaccgac atccttacg              49

SEQ ID NO: 15           moltype =   length =
```

```
SEQUENCE: 15
000

SEQ ID NO: 16          moltype =   length =
SEQUENCE: 16
000

SEQ ID NO: 17          moltype =   length =
SEQUENCE: 17
000

SEQ ID NO: 18          moltype = RNA  length = 22
FEATURE                Location/Qualifiers
source                 1..22
                       mol_type = other RNA
                       organism = synthetic construct
misc_feature           1..22
                       note = Synthetic Oligonucleotide
SEQUENCE: 18
ggtggatttg tgcgacacca cc                                   22

SEQ ID NO: 19          moltype = RNA  length = 27
FEATURE                Location/Qualifiers
source                 1..27
                       mol_type = other RNA
                       organism = synthetic construct
misc_feature           1..27
                       note = Synthetic Oligonucleotide
SEQUENCE: 19
atgggaatgg cgccgtggat ggcccat                              27

SEQ ID NO: 20          moltype =   length =
SEQUENCE: 20
000

SEQ ID NO: 21          moltype = RNA  length = 25
FEATURE                Location/Qualifiers
source                 1..25
                       mol_type = other RNA
                       organism = synthetic construct
misc_feature           1..25
                       note = Synthetic Oligonucleotide
SEQUENCE: 21
ggcagagacg tatgggcctg ctgcc                                25

SEQ ID NO: 22          moltype =   length =
SEQUENCE: 22
000

SEQ ID NO: 23          moltype = DNA  length = 52
FEATURE                Location/Qualifiers
misc_feature           1..52
                       note = Synthetic Oligonucleotide
misc_feature           20..52
                       note = 3' Tail
source                 1..52
                       mol_type = other DNA
                       organism = synthetic construct
SEQUENCE: 23
tcggtatcgg gtgcttgaat ttaaaaaaaa aaaaaaaaaa aaaaaaaaaa aa  52

SEQ ID NO: 24          moltype = DNA  length = 53
FEATURE                Location/Qualifiers
misc_feature           1..53
                       note = Synthetic Oligonucleotide
misc_feature           21..53
                       note = 3' Tail
source                 1..53
                       mol_type = other DNA
                       organism = synthetic construct
SEQUENCE: 24
agatcggtat cgggtgcttg tttaaaaaaa aaaaaaaaaa aaaaaaaaaa aaa 53

SEQ ID NO: 25          moltype =   length =
SEQUENCE: 25
000

SEQ ID NO: 26          moltype = DNA  length = 21
FEATURE                Location/Qualifiers
```

```
misc_feature           1..21
                       note = Synthetic Oligonucleotide
source                 1..21
                       mol_type = other DNA
                       organism = synthetic construct
SEQUENCE: 26
cgttacaaga aatatacacg g                                          21

SEQ ID NO: 27          moltype = RNA  length = 28
FEATURE                Location/Qualifiers
source                 1..28
                       mol_type = other RNA
                       organism = synthetic construct
misc_feature           1..28
                       note = Synthetic Oligonucleotide
SEQUENCE: 27
ggaatggcgc cgtggatggt tgcattgg                                   28

SEQ ID NO: 28          moltype = RNA  length = 23
FEATURE                Location/Qualifiers
source                 1..23
                       mol_type = other RNA
                       organism = synthetic construct
misc_feature           1..23
                       note = Synthetic Oligonucleotide
SEQUENCE: 28
gccgtcagcc aaccatccac ggc                                        23

SEQ ID NO: 29          moltype =   length =
SEQUENCE: 29
000

SEQ ID NO: 30          moltype =   length =
SEQUENCE: 30
000

SEQ ID NO: 31          moltype = DNA  length = 17
FEATURE                Location/Qualifiers
misc_feature           1..17
                       note = Synthetic Oligonucleotide
source                 1..17
                       mol_type = other DNA
                       organism = synthetic construct
SEQUENCE: 31
ggcgttacaa gaaatat                                               17

SEQ ID NO: 32          moltype = DNA  length = 19
FEATURE                Location/Qualifiers
misc_feature           1..19
                       note = Synthetic Oligonucleotide
source                 1..19
                       mol_type = other DNA
                       organism = synthetic construct
SEQUENCE: 32
gcggcgttac aagaaatat                                             19

SEQ ID NO: 33          moltype =   length =
SEQUENCE: 33
000

SEQ ID NO: 34          moltype = DNA  length = 21
FEATURE                Location/Qualifiers
misc_feature           1..21
                       note = Synthetic Oligonucleotide
source                 1..21
                       mol_type = other DNA
                       organism = synthetic construct
SEQUENCE: 34
ggtagtttgg cttttctttg g                                          21

SEQ ID NO: 35          moltype =   length =
SEQUENCE: 35
000

SEQ ID NO: 36          moltype = DNA  length = 58
FEATURE                Location/Qualifiers
misc_feature           1..58
                       note = Synthetic Oligonucleotide
misc_feature           26..58
```

```
                        note = 3' Tail
source                  1..58
                        mol_type = other DNA
                        organism = synthetic construct
SEQUENCE: 36
ggatggagcg taccaccgaa tttcctttaa aaaaaaaaaa aaaaaaaaaa aaaaaaaa    58

SEQ ID NO: 37           moltype = DNA  length = 53
FEATURE                 Location/Qualifiers
misc_feature            1..53
                        note = Synthetic Oligonucleotide
misc_feature            21..53
                        note = 3' Tail
source                  1..53
                        mol_type = other DNA
                        organism = synthetic construct
SEQUENCE: 37
taccaccgaa tttcccaccc tttaaaaaaa aaaaaaaaaa aaaaaaaaaa aaa         53

SEQ ID NO: 38           moltype =   length =
SEQUENCE: 38
000

SEQ ID NO: 39           moltype =   length =
SEQUENCE: 39
000

SEQ ID NO: 40           moltype =   length =
SEQUENCE: 40
000

SEQ ID NO: 41           moltype =   length =
SEQUENCE: 41
000

SEQ ID NO: 42           moltype =   length =
SEQUENCE: 42
000

SEQ ID NO: 43           moltype =   length =
SEQUENCE: 43
000

SEQ ID NO: 44           moltype =   length =
SEQUENCE: 44
000

SEQ ID NO: 45           moltype = RNA  length = 28
FEATURE                 Location/Qualifiers
source                  1..28
                        mol_type = other RNA
                        organism = synthetic construct
misc_feature            1..28
                        note = Synthetic Oligonucleotide
SEQUENCE: 45
catgcgcttt tctgagaagc aacgcatg                                     28

SEQ ID NO: 46           moltype = RNA  length = 30
FEATURE                 Location/Qualifiers
source                  1..30
                        mol_type = other RNA
                        organism = synthetic construct
misc_feature            1..30
                        note = Synthetic Oligonucleotide
SEQUENCE: 46
ctgagaagca acttctctat taacgctcag                                   30

SEQ ID NO: 47           moltype =   length =
SEQUENCE: 47
000

SEQ ID NO: 48           moltype = DNA  length = 59
FEATURE                 Location/Qualifiers
misc_feature            1..59
                        note = Synthetic Oligonucleotide
misc_feature            27..59
                        note = 3' Tail
source                  1..59
                        mol_type = other DNA
```

```
                        organism = synthetic construct
SEQUENCE: 48
gctcagaaaa ccagaagcga aacgggttta aaaaaaaaaa aaaaaaaaaa aaaaaaaaa   59

SEQ ID NO: 49           moltype =   length =
SEQUENCE: 49
000

SEQ ID NO: 50           moltype =   length =
SEQUENCE: 50
000

SEQ ID NO: 51           moltype =   length =
SEQUENCE: 51
000

SEQ ID NO: 52           moltype =   length =
SEQUENCE: 52
000

SEQ ID NO: 53           moltype =   length =
SEQUENCE: 53
000

SEQ ID NO: 54           moltype =   length =
SEQUENCE: 54
000

SEQ ID NO: 55           moltype =   length =
SEQUENCE: 55
000

SEQ ID NO: 56           moltype =   length =
SEQUENCE: 56
000

SEQ ID NO: 57           moltype =   length =
SEQUENCE: 57
000

SEQ ID NO: 58           moltype =   length =
SEQUENCE: 58
000

SEQ ID NO: 59           moltype =   length =
SEQUENCE: 59
000

SEQ ID NO: 60           moltype = RNA  length = 22
FEATURE                 Location/Qualifiers
source                  1..22
                        mol_type = other RNA
                        organism = synthetic construct
misc_feature            1..22
                        note = Synthetic Oligonucleotide
SEQUENCE: 60
ggatgtgact gtcatgccat cc                                           22

SEQ ID NO: 61           moltype =   length =
SEQUENCE: 61
000

SEQ ID NO: 62           moltype =   length =
SEQUENCE: 62
000

SEQ ID NO: 63           moltype =   length =
SEQUENCE: 63
000

SEQ ID NO: 64           moltype = RNA  length = 26
FEATURE                 Location/Qualifiers
source                  1..26
                        mol_type = other RNA
                        organism = synthetic construct
misc_feature            1..26
                        note = Synthetic Oligonucleotide
SEQUENCE: 64
gaatggcgcc gtggatggtt gcattc                                       26
```

```
SEQ ID NO: 65          moltype = DNA  length = 53
FEATURE                Location/Qualifiers
misc_feature           1..53
                       note = Synthetic Oligonucleotide
misc_feature           21..53
                       note = 3' Tail
source                 1..53
                       mol_type = other DNA
                       organism = synthetic construct
SEQUENCE: 65
agatcggtat cgggtgcttg tttaaaaaaa aaaaaaaaaa aaaaaaaaaa aaa         53

SEQ ID NO: 66          moltype = DNA  length = 50
FEATURE                Location/Qualifiers
misc_feature           1..50
                       note = Synthetic Oligonucleotide
misc_feature           18..50
                       note = 3' Tail
source                 1..50
                       mol_type = other DNA
                       organism = synthetic construct
SEQUENCE: 66
gatggagcgt accaccgttt aaaaaaaaaa aaaaaaaaaa aaaaaaaaaa             50

SEQ ID NO: 67          moltype = DNA  length = 49
FEATURE                Location/Qualifiers
misc_feature           1..49
                       note = Synthetic Oligonucleotide
misc_feature           17..49
                       note = 3' Tail
source                 1..49
                       mol_type = other DNA
                       organism = synthetic construct
SEQUENCE: 67
cggtatcggg tgcttgttta aaaaaaaaaa aaaaaaaaaa aaaaaaaaa              49

SEQ ID NO: 68          moltype =   length =
SEQUENCE: 68
000

SEQ ID NO: 69          moltype = DNA  length = 49
FEATURE                Location/Qualifiers
misc_feature           1..49
                       note = Synthetic Oligonucleotide
misc_feature           17..49
                       note = 3' Tail
source                 1..49
                       mol_type = other DNA
                       organism = synthetic construct
SEQUENCE: 69
ccagaagcga aacgggttta aaaaaaaaaa aaaaaaaaaa aaaaaaaaa              49

SEQ ID NO: 70          moltype =   length =
SEQUENCE: 70
000

SEQ ID NO: 71          moltype =   length =
SEQUENCE: 71
000

SEQ ID NO: 72          moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 72
gctgtaaaag gcttacttcg                                              20

SEQ ID NO: 73          moltype = DNA  length = 21
FEATURE                Location/Qualifiers
misc_feature           1..21
                       note = Synthetic Oligonucleotide
source                 1..21
                       mol_type = other DNA
                       organism = synthetic construct
SEQUENCE: 73
```

```
cttccttagc gtgaaaacgc a                                           21

SEQ ID NO: 74          moltype = DNA  length = 23
FEATURE                Location/Qualifiers
misc_feature           1..23
                       note = Synthetic Oligonucleotide
source                 1..23
                       mol_type = other DNA
                       organism = synthetic construct
SEQUENCE: 74
aggctgtaaa aggtctgctt cgt                                         23

SEQ ID NO: 75          moltype = DNA  length = 19
FEATURE                Location/Qualifiers
misc_feature           1..19
                       note = Synthetic Oligonucleotide
source                 1..19
                       mol_type = other DNA
                       organism = synthetic construct
SEQUENCE: 75
agaaatcttc agagcccga                                              19

SEQ ID NO: 76          moltype =   length =
SEQUENCE: 76
000

SEQ ID NO: 77          moltype = DNA  length = 19
FEATURE                Location/Qualifiers
misc_feature           1..19
                       note = Synthetic Oligonucleotide
source                 1..19
                       mol_type = other DNA
                       organism = synthetic construct
SEQUENCE: 77
tcaagttcgc atattgcac                                              19

SEQ ID NO: 78          moltype =   length =
SEQUENCE: 78
000

SEQ ID NO: 79          moltype = DNA  length = 18
FEATURE                Location/Qualifiers
misc_feature           1..18
                       note = Synthetic Oligonucleotide
source                 1..18
                       mol_type = other DNA
                       organism = synthetic construct
SEQUENCE: 79
accgacatcc ttacgtag                                               18

SEQ ID NO: 80          moltype = DNA  length = 22
FEATURE                Location/Qualifiers
misc_feature           1..22
                       note = Synthetic Oligonucleotide
source                 1..22
                       mol_type = other DNA
                       organism = synthetic construct
SEQUENCE: 80
atactggacc gacatcctta cg                                          22

SEQ ID NO: 81          moltype =   length =
SEQUENCE: 81
000

SEQ ID NO: 82          moltype =   length =
SEQUENCE: 82
000

SEQ ID NO: 83          moltype =   length =
SEQUENCE: 83
000

SEQ ID NO: 84          moltype = DNA  length = 20
FEATURE                Location/Qualifiers
misc_feature           1..20
                       note = Synthetic Oligonucleotide
source                 1..20
                       mol_type = other DNA
                       organism = synthetic construct
```

```
SEQUENCE: 84
agatcggtat cgggtgcttg                                        20

SEQ ID NO: 85          moltype =   length =
SEQUENCE: 85
000

SEQ ID NO: 86          moltype =   length =
SEQUENCE: 86
000

SEQ ID NO: 87          moltype = DNA  length = 26
FEATURE                Location/Qualifiers
misc_feature           1..26
                       note = Synthetic Oligonucleotide
source                 1..26
                       mol_type = other DNA
                       organism = synthetic construct
SEQUENCE: 87
gctcagaaaa ccagaagcga aacggg                                 26

SEQ ID NO: 88          moltype =   length =
SEQUENCE: 88
000

SEQ ID NO: 89          moltype = RNA  length = 20
FEATURE                Location/Qualifiers
source                 1..20
                       mol_type = other RNA
                       organism = synthetic construct
misc_feature           1..20
                       note = Synthetic Oligonucleotide
SEQUENCE: 89
agatcggtat cgggtgcttg                                        20

SEQ ID NO: 90          moltype = DNA  length = 17
FEATURE                Location/Qualifiers
misc_feature           1..17
                       note = Synthetic Oligonucleotide
source                 1..17
                       mol_type = other DNA
                       organism = synthetic construct
SEQUENCE: 90
gatggagcgt accaccg                                           17

SEQ ID NO: 91          moltype = DNA  length = 16
FEATURE                Location/Qualifiers
misc_feature           1..16
                       note = Synthetic Oligonucleotide
source                 1..16
                       mol_type = other DNA
                       organism = synthetic construct
SEQUENCE: 91
cggtatcggg tgcttg                                            16

SEQ ID NO: 92          moltype =   length =
SEQUENCE: 92
000

SEQ ID NO: 93          moltype = DNA  length = 16
FEATURE                Location/Qualifiers
misc_feature           1..16
                       note = Synthetic Oligonucleotide
source                 1..16
                       mol_type = other DNA
                       organism = synthetic construct
SEQUENCE: 93
ccagaagcga aacggg                                            16

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
```

```
000

SEQ ID NO: 97          moltype =   length =
SEQUENCE: 97
000

SEQ ID NO: 98          moltype = DNA  length = 19
FEATURE                Location/Qualifiers
misc_feature           1..19
                       note = Synthetic Oligonucleotide
source                 1..19
                       mol_type = other DNA
                       organism = synthetic construct
SEQUENCE: 98
tcggtatcgg gtgcttgaa                                              19

SEQ ID NO: 99          moltype = DNA  length = 25
FEATURE                Location/Qualifiers
misc_feature           1..25
                       note = Synthetic Oligonucleotide
source                 1..25
                       mol_type = other DNA
                       organism = synthetic construct
SEQUENCE: 99
ggatggagcg taccaccgaa tttcc                                       25

SEQ ID NO: 100         moltype = DNA  length = 20
FEATURE                Location/Qualifiers
misc_feature           1..20
                       note = Synthetic Oligonucleotide
source                 1..20
                       mol_type = other DNA
                       organism = synthetic construct
SEQUENCE: 100
taccaccgaa tttcccaccc                                             20

SEQ ID NO: 101         moltype =   length =
SEQUENCE: 101
000

SEQ ID NO: 102         moltype = RNA  length = 20
FEATURE                Location/Qualifiers
source                 1..20
                       mol_type = other RNA
                       organism = synthetic construct
misc_feature           1..20
                       note = Synthetic Oligonucleotide
SEQUENCE: 102
ccaagtcctt gtggcttggc                                             20

SEQ ID NO: 103         moltype =   length =
SEQUENCE: 103
000

SEQ ID NO: 104         moltype =   length =
SEQUENCE: 104
000

SEQ ID NO: 105         moltype =   length =
SEQUENCE: 105
000

SEQ ID NO: 106         moltype = RNA  length = 17
FEATURE                Location/Qualifiers
source                 1..17
                       mol_type = other RNA
                       organism = synthetic construct
misc_feature           1..17
                       note = Synthetic Oligonucleotide
SEQUENCE: 106
ggtggatttg tgcgaca                                                17

SEQ ID NO: 107         moltype = RNA  length = 22
FEATURE                Location/Qualifiers
source                 1..22
                       mol_type = other RNA
                       organism = synthetic construct
misc_feature           1..22
                       note = Synthetic Oligonucleotide
```

```
SEQUENCE: 107
atgggaatgg cgccgtggat gg                                            22

SEQ ID NO: 108          moltype = RNA  length = 20
FEATURE                 Location/Qualifiers
source                  1..20
                        mol_type = other RNA
                        organism = synthetic construct
misc_feature            1..20
                        note = Synthetic Oligonucleotide
SEQUENCE: 108
ggcagagacg tatgggcctg                                               20

SEQ ID NO: 109          moltype = RNA  length = 22
FEATURE                 Location/Qualifiers
source                  1..22
                        mol_type = other RNA
                        organism = synthetic construct
misc_feature            1..22
                        note = Synthetic Oligonucleotide
SEQUENCE: 109
ggaatggcgc cgtggatggt tg                                            22

SEQ ID NO: 110          moltype = RNA  length = 18
FEATURE                 Location/Qualifiers
source                  1..18
                        mol_type = other RNA
                        organism = synthetic construct
misc_feature            1..18
                        note = Synthetic Oligonucleotide
SEQUENCE: 110
cagccaacca tccacggc                                                 18

SEQ ID NO: 111          moltype =   length =
SEQUENCE: 111
000

SEQ ID NO: 112          moltype =   length =
SEQUENCE: 112
000

SEQ ID NO: 113          moltype = RNA  length = 23
FEATURE                 Location/Qualifiers
source                  1..23
                        mol_type = other RNA
                        organism = synthetic construct
misc_feature            1..23
                        note = Synthetic Oligonucleotide
SEQUENCE: 113
catgcgcttt tctgagaagc aac                                           23

SEQ ID NO: 114          moltype = RNA  length = 25
FEATURE                 Location/Qualifiers
source                  1..25
                        mol_type = other RNA
                        organism = synthetic construct
misc_feature            1..25
                        note = Synthetic Oligonucleotide
SEQUENCE: 114
ctgagaagca acttctctat taacg                                         25

SEQ ID NO: 115          moltype =   length =
SEQUENCE: 115
000

SEQ ID NO: 116          moltype =   length =
SEQUENCE: 116
000

SEQ ID NO: 117          moltype =   length =
SEQUENCE: 117
000

SEQ ID NO: 118          moltype =   length =
SEQUENCE: 118
000

SEQ ID NO: 119          moltype =   length =
SEQUENCE: 119
```

```
000

SEQ ID NO: 120         moltype =   length =
SEQUENCE: 120
000

SEQ ID NO: 121         moltype =   length =
SEQUENCE: 121
000

SEQ ID NO: 122         moltype =   length =
SEQUENCE: 122
000

SEQ ID NO: 123         moltype =   length =
SEQUENCE: 123
000

SEQ ID NO: 124         moltype = RNA  length = 17
FEATURE                Location/Qualifiers
source                 1..17
                       mol_type = other RNA
                       organism = synthetic construct
misc_feature           1..17
                       note = Synthetic Oligonucleotide
SEQUENCE: 124
ggatgtgact gtcatgc                                                17

SEQ ID NO: 125         moltype =   length =
SEQUENCE: 125
000

SEQ ID NO: 126         moltype =   length =
SEQUENCE: 126
000

SEQ ID NO: 127         moltype =   length =
SEQUENCE: 127
000

SEQ ID NO: 128         moltype = RNA  length = 21
FEATURE                Location/Qualifiers
source                 1..21
                       mol_type = other RNA
                       organism = synthetic construct
misc_feature           1..21
                       note = Synthetic Oligonucleotide
SEQUENCE: 128
gaatggcgcc gtggatggtt g                                           21

SEQ ID NO: 129         moltype = DNA  length = 308
FEATURE                Location/Qualifiers
source                 1..308
                       mol_type = genomic DNA
                       organism = Candida albicans
SEQUENCE: 129
ccggtcaaca taaggagttt tctttagaaa ctcattcaca accaaatgcg ggtgggaaat  60
tcggtggtac gctccatcct ttacagattt gctcctgaga gcttcttcct tagcgtgaaa  120
gcgcatgggc ggcgttacaa gaaatataca cggagtttta aggctgtaga aggtctgctt  180
cgtatgggaa tggcgccgtg gatggttggc tgtgagtaat tctttactac aagctgttta  240
gtgcaatatg cgaacttgaa gtcaccttca agcacccgat accgatcacc gacttgagac  300
aggtttta                                                          308

SEQ ID NO: 130         moltype = DNA  length = 365
FEATURE                Location/Qualifiers
source                 1..365
                       mol_type = genomic DNA
                       organism = Candida parapsilosis
SEQUENCE: 130
gagctcgact cgtctcgatt cgcattgacc cgcgaacaaa aggaactttc cgttcaaaag  60
caaaaattat gcgggtggga aattcggtgg tactctccat tcattcaaga tttgtgctcc  120
tgagagcaaa ttcctgagcg tgcaaacgca tgggcggtgt taaaagaaat cttcagagcc  180
cgaaggcgcc cgactacctt cggtagtttg gcttttcttt gggttctatg ggaatgacgc  240
cgtgaatggt tggctgttgt ttagtgtcaa agcgaacaag ggctatttag tgcaatatgc  300
gaacttgatg gttgttcata actgtcaaga acccgatacc gatcattgac gatgagttga  360
gttaa                                                             365

SEQ ID NO: 131         moltype = DNA  length = 1008
FEATURE                Location/Qualifiers
```

```
source                 1..1008
                       mol_type = genomic DNA
                       organism = Candida glabrata
SEQUENCE: 131
ggattacagc ttagtggagc ttggagtata ggtgctcctc tgagttcatt ttgagcctct  60
gggtactctt gagagtactg actcttacgc ggttggttac atgtggtttg aaggtctttt  120
ctgagggttt ttctgttgga ggttacggga gttgtgtgtg tcggtgtatt gtcgtggagc  180
ttcacttgga gttgtctgcg tctcagagca agtcgtgggg attatgtctt ttggctgtcc  240
gttcgttttc ctcttcacct ttctgcttgt acaataggtc ttgtagagct ccagtgctat  300
tcttagtcga ccgtgaggac ggctttcggg ggaacccggc cggtaagatt aagtgcattg  360
gagtttctgc tgaaatctgt atcgtataag gaggataagg gtggggcaga gacgtatggg  420
cctgtctagg gatgtgactg tcatgcgctt ttctgagaag caacttctct attaacggtg  480
gatttgtgcg acacttctcc attgctcact tcctctctaa tggagggccc tacgtaagga  540
tgtcggtcca gtatgtctgc gattgtttct gtggtggacc tcgcgctgtt ataagaaata  600
tacccgtttc gcttctggtt ttctgagcag gaagatatat ttccagtgaa gatgcaccag  660
gagcaacggc tgggaatggc agcggattaa gaaagccact gaaaactctc gcaggtgcat  720
tgggtagaga aagcctgcgt attttctttc cacatattcc tacatcacta tgaagggtgg  780
agctttcctc tcttcagaga tgttccgtag ttctctgggg tgcttagttt gatcatgtgg  840
tgcgtcttct tcttagtttc acggcttggc tcacacactt tgtcgcttta aacctgccat  900
ttccgctctc ttaagagagt gcattggtgt gaggcgaggt gtcaaaatcg tggtgaggct  960
ttattcagtg caattgtagg acttgtcgtc tcgttagaga tgatttga              1008

SEQ ID NO: 132         moltype = DNA  length = 25
FEATURE                Location/Qualifiers
misc_feature           1..25
                       note = Synthetic Oligonucleotide
source                 1..25
                       mol_type = other DNA
                       organism = synthetic construct
SEQUENCE: 132
gcggcgttac aagaaatata cacgg                                       25

SEQ ID NO: 133         moltype = DNA  length = 14
FEATURE                Location/Qualifiers
misc_feature           1..14
                       note = Synthetic Oligonucleotide
source                 1..14
                       mol_type = other DNA
                       organism = synthetic construct
SEQUENCE: 133
gttacaagaa atat                                                   14

SEQ ID NO: 134         moltype = DNA  length = 25
FEATURE                Location/Qualifiers
misc_feature           1..25
                       note = Synthetic Oligonucleotide
source                 1..25
                       mol_type = other DNA
                       organism = synthetic construct
SEQUENCE: 134
atactggacc gacatcctta cgtag                                       25

SEQ ID NO: 135         moltype = DNA  length = 15
FEATURE                Location/Qualifiers
misc_feature           1..15
                       note = Synthetic Oligonucleotide
source                 1..15
                       mol_type = other DNA
                       organism = synthetic construct
SEQUENCE: 135
accgacatcc ttacg                                                  15

SEQ ID NO: 136         moltype = DNA  length = 21
FEATURE                Location/Qualifiers
misc_feature           1..21
                       note = Synthetic Oligonucleotide
source                 1..21
                       mol_type = other DNA
                       organism = synthetic construct
SEQUENCE: 136
agtgcattgg agtttctgct g                                           21

SEQ ID NO: 137         moltype = DNA  length = 16
FEATURE                Location/Qualifiers
misc_feature           1..16
                       note = Synthetic Oligonucleotide
source                 1..16
                       mol_type = other DNA
                       organism = synthetic construct
```

```
SEQUENCE: 137
gcattggagt ttctgc                                                   16

SEQ ID NO: 138          moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 138
agatcggtat cgggtgcttg aa                                            22

SEQ ID NO: 139          moltype = DNA  length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 139
cggtatcggg tgcttg                                                   16

SEQ ID NO: 140          moltype = DNA  length = 30
FEATURE                 Location/Qualifiers
misc_feature            1..30
                        note = Synthetic Oligonucleotide
source                  1..30
                        mol_type = other DNA
                        organism = synthetic construct
SEQUENCE: 140
ggatggagcg taccaccgaa tttcccaccc                                    30

SEQ ID NO: 141          moltype =   length =
SEQUENCE: 141
000

SEQ ID NO: 142          moltype = DNA  length = 42
FEATURE                 Location/Qualifiers
misc_feature            1..42
                        note = Synthetic Oligonucleotide
source                  1..42
                        mol_type = other DNA
                        organism = synthetic construct
SEQUENCE: 142
ggaaatatat cttcctgctc agaaaaccag aagcgaaacg gg                      42

SEQ ID NO: 143          moltype = DNA  length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 143
ccagaagcga aacggg                                                   16

SEQ ID NO: 144          moltype =   length =
SEQUENCE: 144
000

SEQ ID NO: 145          moltype = RNA  length = 29
FEATURE                 Location/Qualifiers
source                  1..29
                        mol_type = other RNA
                        organism = synthetic construct
misc_feature            1..29
                        note = Synthetic Oligonucleotide
SEQUENCE: 145
atgggaatgg cgccgtggat ggttggctg                                     29

SEQ ID NO: 146          moltype = RNA  length = 14
FEATURE                 Location/Qualifiers
source                  1..14
                        mol_type = other RNA
                        organism = synthetic construct
misc_feature            1..14
                        note = Synthetic Oligonucleotide
SEQUENCE: 146
```

```
gccgtggatg gttg                                                 14

SEQ ID NO: 147          moltype = RNA  length = 35
FEATURE                 Location/Qualifiers
source                  1..35
                        mol_type = other RNA
                        organism = synthetic construct
misc_feature            1..35
                        note = Synthetic Oligonucleotide
SEQUENCE: 147
ggatgtgact gtcatgcgct tttctgagaa gcaac                          35

SEQ ID NO: 148          moltype =   length =
SEQUENCE: 148
000

SEQ ID NO: 149          moltype = RNA  length = 23
FEATURE                 Location/Qualifiers
source                  1..23
                        mol_type = other RNA
                        organism = synthetic construct
misc_feature            1..23
                        note = Synthetic Oligonucleotide
SEQUENCE: 149
gccgtggatg gttggctgac ggc                                       23

SEQ ID NO: 150          moltype = RNA  length = 18
FEATURE                 Location/Qualifiers
source                  1..18
                        mol_type = other RNA
                        organism = synthetic construct
misc_feature            1..18
                        note = Synthetic Oligoncleotide
SEQUENCE: 150
gccgtggatg gttggctg                                             18

SEQ ID NO: 151          moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 151
gctgtaaaag gyytrcttcg                                           20

SEQ ID NO: 152          moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 152
aggctgtaaa aggyytrctt cgt                                       23

SEQ ID NO: 153          moltype = DNA  length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 153
gtgaaagcgc atgggc                                               16

SEQ ID NO: 154          moltype = DNA  length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 154
gaaatcttca gagcccgaag g                                         21

SEQ ID NO: 155          moltype = RNA  length = 28
FEATURE                 Location/Qualifiers
source                  1..28
```

-continued

```
                    mol_type = other RNA
                    organism = synthetic construct
misc_feature        1..28
                    note = Synthetic Oligonucleotide
SEQUENCE: 155
ggaatggcgc cgtggatggt tgcattcc                           28
```

PROBES FOR DETECTING *CANDIDA GLABRATA*

CROSS-REFERENCE TO RELATED APPLICATIONS

This application is a divisional of U.S. patent application Ser. No. 17/371,274, filed Jul. 9, 2021, which is a continuation of U.S. patent application Ser. No. 16/065,461, filed Jun. 22, 2018, now issued as U.S. Pat. No. 11,111,549, which is a national stage entry of International Application No. PCT/US2017/012163, filed Jan. 4, 2017, which claims benefit of priority under 35 U.S.C § 119(e) to U.S. Provisional Application No. 62/274,610, filed Jan. 4, 2016. Each of the foregoing applications is hereby incorporated by reference herein in its entirety.

REFERENCE TO SEQUENCE LISTING

The instant application contains a Sequence Listing which has been submitted electronically in XML format and is hereby incorporated by reference in its entirety. Said XML Copy, created on Jan. 23, 2025, is named "4340-P14US-DIV3 Seq Listing ST26" and is 125,624 bytes in size.

BACKGROUND

Genital/vulvovaginal candidiasis (VVC) is also sometimes called a "yeast infection." It is a common infection that occurs when there is overgrowth of the yeast called *Candida. Candida* is always present in and on the body in small amounts. However, when an imbalance occurs, such as when the normal acidity of the vagina changes or when hormonal balance changes, *Candida* can multiply. When that happens, symptoms of candidiasis may appear.

Women with VVC usually experience genital itching, burning, and sometimes a "cottage cheese-like" vaginal discharge. Men with genital candidiasis may experience an itchy rash on the penis. The symptoms of VVC are similar to those of many other genital infections, so it is important to receive a proper diagnosis to assure proper treatment.

There is at present no single criterion for diagnosis of VVC. Diagnosis must be based on the clinical assessment of a number of indications, both from laboratory findings and the patient's condition. It can be difficult to diagnose a yeast infection by physical examination only. Usually the diagnosis is made by taking a sample of the vaginal secretions and looking at the sample under a microscope to see if an abnormal number of *Candida* organisms are present. A fungal culture may not always be useful because *Candida* species are normal inhabitants of the body.

Treatment of *Candida* infections is often delayed until the causative organism is identified because the antifungal drugs used have host toxicity, yet there is a much improved prognosis if antifungal therapy is prompt. The focus of any treatment regime is therefore on the specificity and rapidity of diagnosis of the infection. There is accordingly a need for a rapid, sensitive and specific test to aid in the diagnosis of the infections such as candidemia caused by pathogenic yeasts.

It is accordingly an object of the present invention to provide compositions, reaction mixtures, methods and kits for the specific, sensitive and rapid detection of *Candida* species in a sample.

SUMMARY

In one aspect, the present invention provides a method for determining the presence or absence of *Candida* sp. in a sample. The method generally includes the following steps:

(1) contacting a sample suspected of containing *Candida* sp. with at least one of a first amplification oligomer combination and a second amplification oligomer combination, where
- (a) the first amplification oligomer combination comprises first and second *Candida*-specific amplification oligomers for amplifying a first *Candida* sp. target nucleic acid region or a second *Candida* sp. target nucleic acid region, where the first target region corresponds to a region of SEQ ID NO:129 from about nucleotide position 133 or 161 to about nucleotide position 259 and the second region corresponds to a region of SEQ ID NO:130 from about nucleotide position 202 to about nucleotide position 308, and where the first and second *Candida*-specific amplification oligomers respectively comprise first and second *Candida*-specific target-hybridizing sequences; and
- (b) the second amplification oligomer combination comprises first and second *C. glabrata*-specific amplification oligomers for amplifying a third *Candida* sp. target nucleic acid region, where the third target region corresponds to a region of SEQ ID NO:131 from about nucleotide position 355 to about nucleotide position 554, and where the first and second *C. glabrata*-specific amplification oligomers respectively comprise first and second *C. glabrata*-specific target-hybridizing sequences;

(2) performing an in vitro nucleic acid amplification reaction, where any *Candida* sp. target nucleic acid, if present in the sample, is used as a template for generating one or more amplification products corresponding to at least one of the first, second, and third target regions; and (3) detecting the presence or absence of the one or more amplification products, thereby determining the presence or absence of *Candida* sp. in the sample.

In some embodiments of a method for determining the presence or absence of *Candida* sp. in a sample as above, the method includes contacting the sample with both the first and second amplification oligomer combinations. For example, in certain variations, the method is a multiplex method that includes contacting the sample with both the first and second amplification oligomer combinations within the same reaction mixture.

In some embodiments of a method as above, the first *Candida*-specific target-hybridizing sequence substantially corresponds to the nucleotide sequence of residues 28-46 of SEQ ID NO:9, and/or the second *Candida*-specific target-hybridizing sequence is (i) a sequence of from 15 to 24 contiguous nucleotides contained in the sequence of SEQ ID NO:132 and that includes at least the sequence of SEQ ID NO:133, (ii) a sequence of from 20 to 23 contiguous nucleotides contained in the sequence of SEQ ID NO:152 and that includes at least the sequence of SEQ ID NO:151, or (iii) a sequence that substantially corresponds to the nucleotide sequence of SEQ ID NO:34.

In some embodiments of a method as above, the first *C. glabrata*-specific target-hybridizing sequence is a sequence of from 15 to 24 contiguous nucleotides contained in the sequence of SEQ ID NO:134 and that includes at least the sequence of SEQ ID NO:135, and/or the second *C. glabrata*-specific target-hybridizing sequence is a sequence of from 16 to 21 contiguous nucleotides contained in the sequence of SEQ ID NO:136 and that includes at least the sequence of SEQ ID NO:137.

In some embodiments of a method as above, the method further includes contacting the sample with a third *Candida*-specific amplification oligomer, where the first and second *Candida*-specific amplification oligomers are for amplifying the first *Candida* sp. target nucleic acid region and the second *Candida*-specific target-hybridizing sequence is a sequence of from 15 to 24 contiguous nucleotides contained in the sequence of SEQ ID NO:134 and that includes at least the sequence of SEQ ID NO:135, and where the first and third *Candida*-specific amplification oligomers are for amplifying the second *Candida* sp. target region and the third *Candida*-specific amplification oligomer comprises a third *Candida*-specific target-hybridizing sequence that substantially corresponds to the nucleotide sequence of SEQ ID NO:34. In some such embodiments, the third *Candida*-specific target-hybridizing sequence comprises or consists of the nucleotide sequence of SEQ ID NO:34.

In some embodiments of a method as above, the first *Candida*-specific target-hybridizing sequence comprises the nucleotide sequence of residues 28-46 of SEQ ID NO:9; the second *Candida*-specific target-hybridizing sequence comprises the nucleotide sequence of SEQ ID NO:26, residues 3-22 of SEQ ID NO:74, or SEQ ID NO:34; the first *C. glabrata*-specific target-hybridizing sequence comprises the nucleotide sequence of residues 28-49 of SEQ ID NO:14; and/or the second *C. glabrata*-specific target-hybridizing sequence comprises the nucleotide sequence of SEQ ID NO:12. In more particular variations, the first *Candida*-specific target-hybridizing sequence consists of the nucleotide sequence of residues 28-46 of SEQ ID NO:9; the second *Candida*-specific target-hybridizing sequence consists of the nucleotide sequence of SEQ ID NO:26, SEQ ID NO:74, or SEQ ID NO:34; the first *C. glabrata*-specific target-hybridizing sequence consists of the nucleotide sequence of residues 28-49 of SEQ ID NO:14; and/or the second *C. glabrata*-specific target-hybridizing sequence consists of the nucleotide sequence of SEQ ID NO:12.

In some embodiments of a method for determining the presence or absence of *Candida* sp. in a sample as above, at least one of the first *Candida*-specific amplification oligomer and the first *C. glabrata*-specific amplification oligomer is a promoter primer or promoter provider further comprising a promoter sequence located 5' to the respective target hybridizing sequence. A particularly suitable promoter sequence is a T7 promoter sequence such as, e.g., a T7 promoter sequence having the sequence shown in residues 1-27 of SEQ ID NO:9. In some such embodiments, the first *Candida*-specific amplification oligomer has the nucleotide sequence of SEQ ID NO:9 and/or the first *C. glabrata*-specific amplification oligomer has the nucleotide sequence of SEQ ID NO:14.

Typically, the method for determining the presence or absence of *Candida* sp. further includes purifying any *Candida* sp. target nucleic acid, if present, from other components in the sample before step (2). In certain embodiments, the purifying step includes contacting the sample with at least one capture probe oligomer comprising a target-hybridizing sequence covalently attached to a sequence or moiety that binds to an immobilized probe. In some such variations, the sample is contacted with a first *Candida*-specific capture probe oligomer and a first *C. glabrata*-specific capture probe oligomer, where the first *Candida*-specific capture probe oligomer comprises a first *Candida*-specific capture probe target-hybridizing sequence that specifically hybridizes to a target sequence within the first or second *Candida* sp. target nucleic acid, where the first *C. glabrata*-specific capture probe oligomer comprises a first *C. glabrata* capture probe target-hybridizing sequence that specifically hybridizes to a target sequence within the third *Candida* sp. target nucleic acid, and where each of the first *Candida*-specific and *C. glabrata*-specific capture probe target-hybridizing sequences is covalently attached to the sequence or moiety that binds to the immobilized probe. Particularly suitable target-hybridizing sequences for the first *Candida*-specific capture probe include sequences that (i) are from 16 to 21 contiguous nucleotides contained in the sequence of SEQ ID NO:138 and include at least the sequence of SEQ ID NO:139 or (ii) are from 15 to 25 contiguous nucleotides contained in the sequence of SEQ ID NO:140 and include at least the sequence of SEQ ID NO:141. Particularly suitable target-hybridizing sequences for the first *C. glabrata*-specific capture probe include sequences that are from 16 to 27 contiguous nucleotides contained in the sequence of SEQ ID NO:142 and include at least the sequence of SEQ ID NO:143 or SEQ ID NO:144.

In some embodiments where the sample is contacted with a first *Candida*-specific capture probe oligomer as above, the method further includes contacting the sample with a second *Candida*-specific capture probe oligomer. In some such variations, the first *Candida*-specific capture probe target-hybridizing sequence is a sequence of from 16 to 21 contiguous nucleotides contained in the sequence of SEQ ID NO:138 and that includes at least the sequence of SEQ ID NO:139, and the second *Candida*-specific capture probe oligomer comprises a second *Candida*-specific capture probe target-hybridizing sequence that specifically hybridizes to a target sequence within the first or second *Candida* sp. target nucleic acid, where the second *Candida*-specific capture probe target-hybridizing sequence is a sequence of from 15 to 25 contiguous nucleotides contained in the sequence of SEQ ID NO:140 and that includes at least the sequence of SEQ ID NO:141. In more specific variations, the second *Candida*-specific capture probe target-hybridizing sequence comprises or consists of the nucleotide sequence of residues 1-17 of SEQ ID NO:66; in some such embodiments, the second *Candida*-specific capture probe oligomer has the nucleotide sequence of SEQ ID NO:66.

In some embodiments where the sample is contacted with a first *Candida*-specific capture probe oligomer and a first *C. glabrata*-specific capture probe oligomer as above, the first *Candida*-specific capture probe target-hybridizing sequence comprises or consists of the nucleotide sequence of residues 1-20 of SEQ ID NO:24 or residues 1-17 of SEQ ID NO:66, and/or the first *C. glabrata*-specific capture probe target-hybridizing sequence comprises or consists of the nucleotide sequence of residues 1-26 of SEQ ID NO:48. In more specific variations, the first *Candida*-specific capture probe oligomer has the nucleotide sequence of SEQ ID NO:24 or SEQ ID NO:66, and/or the first *C. glabrata*-specific capture probe oligomer has the nucleotide sequence of SEQ ID NO:48.

In certain embodiments, the detecting step (3) includes contacting one or more amplification products with a *Candida*-specific detection probe that specifically hybridizes to the first or second *Candida* sp. target region and a *C. glabrata*-specific detection probe that specifically hybridizes to the third *Candida* sp. target region, and detecting the presence or absence of any target-hybridized *Candida*-specific and/or *C. glabrata*-specific detection probe. Particularly suitable *Candida*-specific detection probes include probes comprising a *Candida*-specific detection probe target-hybridizing sequence selected from (A1) a sequence of from 18 to 22 contiguous nucleotides contained in the sequence of SEQ ID NO:145 and that includes at least the sequence of SEQ ID NO:146, (B1) the DNA equivalent or an RNA/DNA chimeric of (A1), and (C1) the full complement of (A1) or (B1). Particularly suitable *C. glabrata*-specific detection probes include probes comprising a *C. glabrata*-specific detection probe target-hybridizing sequence selected from (A2) a sequence of from 17 to 23 contiguous nucleotides contained in the sequence of SEQ ID NO:147 and that includes at least the sequence of SEQ ID NO:148, (B2) a sequence that substantially corresponds to the sequence of residues 1-17 of SEQ ID NO:18, (C2) a sequence that substantially corresponds to the sequence of residues 1-20 of SEQ ID NO:21, (D2) the DNA equivalent or an RNA/DNA chimeric of any one of (A2)-(C2), and (E2) the full complement of any one of (A2)-(D2). In some embodiments, the *Candida*-specific detection probe target-hybridizing sequence comprises or consists of the sequence of residues 1-22 of SEQ ID NO:27, the DNA equivalent or an RNA/DNA chimeric thereof, or the full complement of any of the foregoing; and/or the *C. glabrata*-specific detection probe target-hybridizing sequence comprises or consists of the sequence of residues 1-17 of SEQ ID NO:60, the sequence of residues 1-23 of SEQ ID NO:45, the sequence of residues 1-17 of SEQ ID NO:18, the sequence of residues 1-20 of SEQ ID NO:21, the DNA equivalent or an RNA/DNA chimeric of any of the foregoing, or the full complement of any of the foregoing. In more specific variations, the *Candida*-specific detection probe has the sequence of SEQ ID NO:27, the DNA equivalent or an RNA/DNA chimeric thereof, or the full complement of any of the foregoing; and/or the *C. glabrata*-specific detection probe has the sequence of SEQ ID NO:60, SEQ ID NO:45, SEQ ID NO:18, SEQ ID NO:21, the DNA equivalent or an RNA/DNA chimeric of any of the foregoing, or the full complement of any of the foregoing.

In some embodiments of a method utilizing a detection probe, each of the *Candida*-specific and *C. glabrata*-specific detection probes includes at least one label. In specific variations, the label is a chemiluminescent label or a fluorescent label. In certain embodiments utilizing a labeled detection probe, the detecting step (3) occurs during the amplifying step (2); in some such embodiments, each of the *Candida*-specific and *C. glabrata*-specific detection probes comprises a fluorescent label and a quencher. Suitable detection probes comprising a fluorescent label and a quencher include molecular torches, a molecular beacons, and TaqMan detection probes.

In some embodiments of a method utilizing a detection probe, at least one of the *Candida*-specific and *C. glabrata*-specific detection probes further includes a non-target-hybridizing sequence. For example, in some variations, each of the *Candida*-specific and *C. glabrata*-specific detection probes is a molecular torch or a molecular beacon.

In certain variations of a method for determining the presence or absence of *Candida* sp. as above, the amplification reaction at step (2) is an isothermal amplification reaction such as, for example, a transcription-mediated amplification (TMA) reaction. In some such embodiments, the amplification reaction is a real-time amplification reaction.

In another aspect, the present invention provides an oligomer combination for determining the presence or absence of *Candida* sp. in a sample. The oligomer combination generally includes at least one of a first amplification oligomer combination and a second amplification oligomer combination, where (a) the first amplification oligomer combination comprises first and second *Candida*-specific amplification oligomers for amplifying a first *Candida* sp. target nucleic acid region or a second *Candida* sp. target nucleic acid region, where the first target region corresponds to a region of SEQ ID NO:129 from about nucleotide position 133 or 161 to about nucleotide position 259 and the second region corresponds to a region of SEQ ID NO:130 from about nucleotide position 202 to about nucleotide position 308, and where the first and second *Candida*-specific amplification oligomers respectively comprise first and second *Candida*-specific target-hybridizing sequences; and (b) the second amplification oligomer combination comprises first and second *C. glabrata*-specific amplification oligomers for amplifying a third *Candida* sp. target nucleic acid region, where the third target region corresponds to a region of SEQ ID NO:131 from about nucleotide position 355 to about nucleotide position 554, and where the first and second *C. glabrata*-specific amplification oligomers respectively comprise first and second *C. glabrata*-specific target-hybridizing sequences.

In some embodiments of an oligomer combination for determining the presence or absence of *Candida* sp. in a sample as above, the oligomer combination includes both the first and second amplification oligomer combinations. For example, in certain variations, the oligomer combination includes both the first and second amplification oligomer combinations within the same reaction mixture.

In some embodiments of an oligomer combination as above, the first *Candida*-specific target-hybridizing sequence substantially corresponds to the nucleotide sequence of residues 28-46 of SEQ ID NO:9, and/or the second *Candida*-specific target-hybridizing sequence is (i) a sequence of from 15 to 24 contiguous nucleotides contained in the sequence of SEQ ID NO:132 and that includes at least the sequence of SEQ ID NO:133, (ii) a sequence of from 20 to 23 contiguous nucleotides contained in the sequence of SEQ ID NO:152 and that includes at least the sequence of SEQ ID NO:151, or (iii) a sequence that substantially corresponds to the nucleotide sequence of SEQ ID NO:34.

In some embodiments of an oligomer combination as above, the first *C. glabrata*-specific target-hybridizing sequence is a sequence of from 15 to 24 contiguous nucleotides contained in the sequence of SEQ ID NO:134 and that includes at least the sequence of SEQ ID NO:135, and/or the second *C. glabrata*-specific target-hybridizing sequence is a sequence of from 16 to 21 contiguous nucleotides contained in the sequence of SEQ ID NO:136 and that includes at least the sequence of SEQ ID NO:137.

In some embodiments of an oligomer combination as above, the oligomer combination further includes a third *Candida*-specific amplification oligomer, where the first and second *Candida*-specific amplification oligomers are for amplifying the first *Candida* sp. target nucleic acid region and the second *Candida*-specific target-hybridizing sequence is a sequence of from 15 to 24 contiguous nucleotides contained in the sequence of SEQ ID NO:134 and that includes at least the sequence of SEQ ID NO:135, and where the first and third *Candida*-specific amplification oligomers are for amplifying the second *Candida* sp. target region and the third *Candida*-specific amplification oligomer comprises a third *Candida*-specific target-hybridizing sequence that substantially corresponds to the nucleotide sequence of SEQ ID NO:34. In some such embodiments, the third *Candida*-specific target-hybridizing sequence comprises or consists of the nucleotide sequence of SEQ ID NO:34.

In some embodiments of an oligomer combination as above, the first *Candida*-specific target-hybridizing sequence comprises the nucleotide sequence of residues 28-46 of SEQ ID NO:9; the second *Candida*-specific target-hybridizing sequence comprises the nucleotide sequence of SEQ ID NO:26, residues 3-22 of SEQ ID NO:74, or SEQ ID NO:34; the first *C. glabrata*-specific target-hybridizing sequence comprises the nucleotide sequence of residues 28-49 of SEQ ID NO:14; and/or the second *C. glabrata*-specific target-hybridizing sequence comprises the nucleotide sequence of SEQ ID NO:12. In more particular variations, the first *Candida*-specific target-hybridizing sequence consists of the nucleotide sequence of residues 28-46 of SEQ ID NO:9; the second *Candida*-specific target-hybridizing sequence consists of the nucleotide sequence of SEQ ID NO:26, SEQ ID NO:74, or SEQ ID NO:34; the first *C. glabrata*-specific target-hybridizing sequence consists of the nucleotide sequence of residues 28-49 of SEQ ID NO:14; and/or the second *C. glabrata*-specific target-hybridizing sequence consists of the nucleotide sequence of SEQ ID NO:12.

In some embodiments of an oligomer combination for determining the presence or absence of *Candida* sp. in a sample as above, at least one of the first *Candida*-specific amplification oligomer and the first *C. glabrata*-specific amplification oligomer is a promoter primer or promoter provider further comprising a promoter sequence located 5' to the respective target hybridizing sequence. A particularly suitable promoter sequence is a T7 promoter sequence such as, e.g., a T7 promoter sequence having the sequence shown in residues 1-27 of SEQ ID NO:9. In some such embodiments, the first *Candida*-specific amplification oligomer has the nucleotide sequence of SEQ ID NO:9 and/or the first *C. glabrata*-specific amplification oligomer has the nucleotide sequence of SEQ ID NO:14.

In certain embodiments, an oligomer combination as above further includes at least one capture probe oligomer comprising a target-hybridizing sequence covalently attached to a sequence or moiety that binds to an immobilized probe. In some such variations, the oligomer combination includes a first *Candida*-specific capture probe oligomer and a first *C. glabrata*-specific capture probe oligomer, where the first *Candida*-specific capture probe oligomer comprises a first *Candida*-specific capture probe target-hybridizing sequence that specifically hybridizes to a target sequence within the first or second *Candida* sp. target nucleic acid, where the first *C. glabrata*-specific capture probe oligomer comprises a first *C. glabrata* capture probe target-hybridizing sequence that specifically hybridizes to a target sequence within the third *Candida* sp. target nucleic acid, and where each of the first *Candida*-specific and *C. glabrata*-specific capture probe target-hybridizing sequences is covalently attached to the sequence or moiety that binds to the immobilized probe. Particularly suitable target-hybridizing sequences for the first *Candida*-specific capture probe include sequences that (i) are from 16 to 21 contiguous nucleotides contained in the sequence of SEQ ID NO:138 and include at least the sequence of SEQ ID NO:139 or (ii) are from 15 to 25 contiguous nucleotides contained in the sequence of SEQ ID NO:140 and include at least the sequence of SEQ ID NO:141. Particularly suitable target-hybridizing sequences for the first *C. glabrata*-specific capture probe include sequences that are from 16 to 27 contiguous nucleotides contained in the sequence of SEQ ID NO:142 and include at least the sequence of SEQ ID NO:143 or SEQ ID NO:144.

In some embodiments where the oligomer combination includes a first *Candida*-specific capture probe oligomer as above, the oligomer combination further includes a second *Candida*-specific capture probe oligomer. In some such variations, the first *Candida*-specific capture probe target-hybridizing sequence is a sequence of from 16 to 21 contiguous nucleotides contained in the sequence of SEQ ID NO:138 and that includes at least the sequence of SEQ ID NO:139, and the second *Candida*-specific capture probe oligomer comprises a second *Candida*-specific capture probe target-hybridizing sequence that specifically hybridizes to a target sequence within the first or second *Candida* sp. target nucleic acid, where the second *Candida*-specific capture probe target-hybridizing sequence is a sequence of from 15 to 25 contiguous nucleotides contained in the sequence of SEQ ID NO:140 and that includes at least the sequence of SEQ ID NO:141. In more specific variations, the second *Candida*-specific capture probe target-hybridizing sequence comprises or consists of the nucleotide sequence of residues 1-17 of SEQ ID NO:66; in some such embodiments, the second *Candida*-specific capture probe oligomer has the nucleotide sequence of SEQ ID NO:66.

In some embodiments where the oligomer combination includes a first *Candida*-specific capture probe oligomer and a first *C. glabrata*-specific capture probe oligomer as above, the first *Candida*-specific capture probe target-hybridizing sequence comprises or consists of the nucleotide sequence of residues 1-20 of SEQ ID NO:24 or residues 1-17 of SEQ ID NO:66, and/or the first *C. glabrata*-specific capture probe target-hybridizing sequence comprises or consists of the nucleotide sequence of residues 1-26 of SEQ ID NO:48. In more specific variations, the first *Candida*-specific capture probe oligomer has the nucleotide sequence of SEQ ID NO:24 or SEQ ID NO:66, and/or the first *C. glabrata*-specific capture probe oligomer has the nucleotide sequence of SEQ ID NO:48.

In certain embodiments, an oligomer combination as above further includes a *Candida*-specific detection probe that specifically hybridizes to the first or second *Candida* sp. target region and a *C. glabrata*-specific detection probe that specifically hybridizes to the third *Candida* sp. target region Particularly suitable *Candida*-specific detection probes include probes comprising a *Candida*-specific detection probe target-hybridizing sequence selected from (A1) a sequence of from 18 to 22 contiguous nucleotides contained in the sequence of SEQ ID NO:145 and that includes at least the sequence of SEQ ID NO:146, (B1) the DNA equivalent or an RNA/DNA chimeric of (A1), and (C1) the full complement of (A1) or (B1). Particularly suitable *C. glabrata*-specific detection probes include probes comprising a *C. glabrata*-specific detection probe target-hybridizing sequence selected from (A2) a sequence of from 17 to 23 contiguous nucleotides contained in the sequence of SEQ ID NO:147 and that includes at least the sequence of SEQ ID NO:148, (B2) a sequence that substantially corresponds to the sequence of residues 1-17 of SEQ ID NO:18, (C2) a sequence that substantially corresponds to the sequence of residues 1-20 of SEQ ID NO:21, (D2) the DNA equivalent or an RNA/DNA chimeric of any one of (A2)-(C2), and (E2) the full complement of any one of (A2)-(D2). In some embodiments, the *Candida*-specific detection probe target-hybridizing sequence comprises or consists of the sequence of residues 1-22 of SEQ ID NO:27, the DNA equivalent or an RNA/DNA chimeric thereof, or the full complement of any of the foregoing; and/or the *C. glabrata*-specific detection probe target-hybridizing sequence comprises or consists of the sequence of residues 1-17 of SEQ ID NO:60, the sequence of residues 1-23 of SEQ ID NO:45, the sequence of residues 1-17 of SEQ ID NO:18, the sequence of residues 1-20 of SEQ ID NO:21, the DNA equivalent or an RNA/DNA chimeric of any of the foregoing, or the full complement of any of the foregoing. In more specific variations, the *Candida*-specific detection probe has the sequence of SEQ ID NO:27, the DNA equivalent or an RNA/DNA chimeric thereof, or the full complement of any of the foregoing; and/or the *C. glabrata*-specific detection probe has the sequence of SEQ ID NO:60, SEQ ID NO:45, SEQ ID NO:18, SEQ ID NO:21, the DNA equivalent or an RNA/DNA chimeric of any of the foregoing, or the full complement of any of the foregoing.

In some embodiments of an oligomer combination further comprising a detection probe, each of the *Candida*-specific and *C. glabrata*-specific detection probes includes at least one label. In specific variations, the label is a chemiluminescent label or a fluorescent label. In some embodiments, each of the *Candida*-specific and *C. glabrata*-specific detection probes comprises a fluorescent label and a quencher. Suitable detection probes comprising a fluorescent label and a quencher include molecular torches, a molecular beacons, and TaqMan detection probes.

In some embodiments of an oligomer combination further comprising a detection probe, at least one of the *Candida*-specific and *C. glabrata*-specific detection probes further includes a non-target-hybridizing sequence. For example, in some variations, each of the *Candida*-specific and *C. glabrata*-specific detection probes is a molecular torch or a molecular beacon.

In another aspect, the present invention provides a detection probe for detecting a *Candida* sp. target nucleic acid, where the detection probe is a *Candida*-specific detection probe or a *C. glabrata*-specific detection probe as described above.

These and other aspects of the invention will become evident upon reference to the following detailed description of the invention.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

"*Candida* sp." as used herein means at least one or more of *C. albicans, C. parapsilosis, C. dubliniensis, C. tropicalis*, and *C. glabrata*. "*Candida*-specific," as used herein in reference to an oligomer, means specificity for at least one or more of *C. albicans, C. parapsilosis, C. dubliniensis*, and *C. tropicalis* target nucleic acid. "*C. glabrata*-specific," as used herein in reference to an oligomer, means specificity for at least *C. glabrata* target nucleic acid.

"Sample" includes any specimen that may contain *Candida* sp. or components thereof, such as nucleic acids or fragments of nucleic acids. Samples include "biological samples" which include any tissue or material derived from a living or dead human that may contain *Candida* sp. or components thereof (e.g., a target nucleic acid derived therefrom), including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11th ed., 1992, Abraham et al., 2007, *BioTechniques* 43: 617-24), which include derivatives of purine or pyrimidine bases (e.g., $N^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Lactobacillus*. It is understood that other reasons exist for configuring a target-hybridizing sequence to have less than 100% complementarity to a target nucleic acid.

The term "targets a sequence," as used herein in reference to a region of *Candida* sp. nucleic acid, refers to a process whereby an oligonucleotide hybridizes to the target sequence in a manner that allows for detection as described herein. In one embodiment, the oligonucleotide is complementary with the targeted *Candida* sp. nucleic acid sequence and contains no mismatches. In another embodiment, the oligonucleotide is complementary but contains 1, 2, 3, 4, or 5 mismatches with the targeted *Candida* sp. nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Candida* sp. target region. Such an oligonucleotide is not limited to targeting that sequence only, but is rather useful as a composition, in a kit or in a method for targeting a *Candida* sp. target nucleic acid. The oligonucleotide is designed to function as a component of an assay for detection of *Candida* sp. from a sample, and therefore is designed to target *Candida* sp. in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to an *Candida* sp. targeted nucleic acid, refers to a piece of contiguous nucleic acid. In certain embodiments, the fragment includes contiguous nucleotides from a non-coding RNA ribozyme that is the RNA component of RNAse P of a *Candida* sp., or contiguous nucleotides of the *Candida* gene RPR1, which encodes the RNA ribozyme component of RNAse P, where the number of contiguous nucleotides in the fragment are less than that for the entire RNA ribozyme encoded by the RPR1 gene.

The term "region," as used herein, refers to a portion of a nucleic acid where the portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is an RNA ribozyme encoded by the RPR1 gene, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein. Variations of transcription-associated amplification are well-known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqMan probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual,* 2nd ed. (Cold Spring Harbor Laboratory Press, Cold Spring Harbor, NY, 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see, e.g., PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-40}$ sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size±5%), to which an immobilized probe is joined directly (via covalent linkage, chelation, or ionic interaction), or indirectly (via one or more linkers), where the linkage or interaction between the probe and support is stable during hybridization conditions.

BRIEF DESCRIPTION OF THE DRAWINGS

FIG. 1 illustrates a reference sequence (SEQ ID NO:129) for *Candida* sp. RPR1 gene (*Candida albicans* strain ATCC 90028 ribonuclease P RNA (RPR1) gene, partial sequence, found at GenBank under accession number DQ660433, GI:110084517, 10 Mar. 2007).

FIG. 2 illustrates a reference sequence (SEQ ID NO:131) for *Candida* sp. RPR1 gene (*Candida glabrata* strain ATCC 2238 ribonuclease P RNA (RPR1) gene, partial sequence, found at GenBank under accession number DQ660434, GI:133874753, 21 Mar. 2007).

FIG. 3 illustrates a reference sequence (SEQ ID NO:130) for *Candida* sp. RPR1 gene (*Candida parapsilosis* strain ATCC 22019 ribonuclease P RNA (RPR1) gene, partial sequence, found at GenBank under accession number DQ660436, GI:110084520, 10 Mar. 2007).

DESCRIPTION

The present invention provides compositions, kits, and methods for determining the presence or absence of *Candida* sp. nucleic acid in a sample. Preferably, the samples are biological samples. The compositions, kits, and methods provide oligonucleotide sequences that recognize target sequences of the RPR1 gene, or the non-coding RNA encoded by the RPR1 gene, including RPR1 target sequences of *C. albicans, C. parapsilosis, C. dubliniensis, C. tropicalis*, and/or *C. glabrata*, or their complementary sequences. Such oligonucleotides may be used as amplification oligonucleotides, which may include primers, promoter primers, and promoter provider oligonucleotides, whose functions have been described previously (see, e.g., U.S. Pat. Nos. 4,683,195; 4,683,202; 4,800,159; 5,399,491; 5,554,516; 5,824,518; and 7,374,885; each incorporated by reference herein). Other oligonucleotides may be used as probes for detecting amplified sequences of *Candida* sp., or for capture of *Candida* sp. target nucleic acid. In certain aspects, a composition of the present invention is a combination of two or more oligomers that recognize *Candida* sp. RPR1 target sequences (e.g., two or more amplification oligomers).

The methods provide for the sensitive and specific detection of *Candida* sp. nucleic acid. In certain embodiments, the methods include performing a nucleic acid amplification of an *Candida* sp. target region and detecting the amplified product by, for example, specifically hybridizing the amplified product with a nucleic acid detection probe that provides a signal to indicate the presence of *Candida* sp. in the sample. The amplification step includes contacting the sample with one or more amplification oligomers specific for a target sequence in a *Candida* sp. target nucleic acid to produce an amplified product if *Candida* sp. nucleic acid is present in the sample. Amplification synthesizes additional copies of the target sequence or its complement by using at least one nucleic acid polymerase and an amplification oligomer to produce the copies from a template strand (e.g., by extending the sequence from a primer using the template strand). One embodiment for detecting the amplified product uses a hybridizing step that includes contacting the amplified product with at least one probe specific for a sequence amplified by the selected amplification oligomers, e.g., a sequence contained in the target sequence flanked by a pair of selected amplification oligomers.

The detection step may be performed using any of a variety of known techniques to detect a signal specifically associated with the amplified target sequence, such as, e.g., by hybridizing the amplification product with a labeled detection probe and detecting a signal resulting from the labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescentally labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

Preferred compositions of the instant invention are configured to specifically hybridize to nucleic acid of at least one of *C. albicans, C. parapsilosis, C. dubliniensis, C. tropicalis*, and/or *C. glabrata* with minimal cross-reactivity to other, non-*Candida* nucleic acids suspected of being in a sample (e.g., other pathogens associated with vaginal infections). In certain variations, compositions (e.g., oligomer combinations) of the invention allow for the detection of a broad range of *Candida* sp. (e.g., any of *C. albicans, C. dubliniensis*, and *C. tropicalis*; any of *C. albicans, C. parapsilosis, C. dubliniensis*, and *C. tropicalis*; or any of *C. albicans, C. parapsilosis, C. dubliniensis, C. tropicalis*, and *C. glabrata*). In some aspects, the compositions of the instant invention are configured to specifically hybridize to nucleic acid of one or more of *C. albicans, C. parapsilosis, C. dubliniensis, C. tropicalis*, and *C. glabrata* with minimal cross-reactivity to one or more of *Trichomonas vaginalis, Chlamydia trachomatis, Acinetobacter iwoffii, Actinomyces israelii, Alcaligenes faecalis, Bacteroides fragilis, Clostridium difficile, Corynebacterium genitalium, Enterobacter cloacae, Enterococcus feacalis, Escherichia coli, Bifidobacterium adolescentis, Campylobacter jejuni, Fusobacterium nucleatum, Haemophilus ducreyi, Klebsiella pneumoniae, Listeria monocytogenes, Mycoplasma hominis, Peptostreptococcus magnus, Propionibacterium acnes, Neisseria gonorrhoeae, Trichomonas vaginalis, Ureaplasma urealyticum, Ureaplasma parvum, Candida krusei, Candida lusitaniae, Prevotella bivia, Eggerthella lenta, Pseudomonas aeruginosa, Mobiluncus curtisii, Chlamydia trachomatis, Cryptococcus neoformans, Staphylococcus aureus, Staphylococcus epidermidis, Streptococcus agalactiae, Streptococcus pyogenes, Leptotrichia bucalis, Proteus vulgaris, Megaspahaera elsdenii, Atopobium vaginae, Lactobacillus acidophilus, Lactobacillus mucosae, Lactobacillus gastricus, Lactobacillus iners, Lactobacillus crispatus, Lactobacillus jensenii, Lactobacillus gasseri*, and *Gardnerella vaginalis*. In some embodiments, the compositions of the instant invention are part of a multiplex system that includes multiple sets of oligomers that, in combination, allow for the detection of any of *C. albicans, C. parapsilosis, C. dubliniensis, C. tropicalis*, and *C. glabrata*, such as in multiplex detection methods as described herein.

In certain aspects of the invention, a combination of at least two oligomers is provided for determining the presence or absence of *Candida* sp. in a sample. Typically, the oligomer combination includes (a) first and second *Candida*-specific amplification oligomers for amplifying a first *Candida* sp. target region corresponding to a region of SEQ ID NO:129 or a second *Candida* sp. target region corresponding to a region of SEQ ID NO:130, and/or (b) first and second *C. glabrata*-specific amplification oligomers for amplifying a third *Candida* sp. target region corresponding to a region of SEQ ID NO:131. In such embodiments, at least one amplification oligomer from each of oligomer set (a) and oligomer set (b) above comprises a target-hybridizing sequence in the sense orientation ("sense THS") and at least one amplification oligomer comprises a target-hybridizing sequence in the antisense orientation ("antisense THS"), where the sense THS and antisense THS of the amplification oligomers of set (a) are each configured to specifically hybridize to a *Candida* sp. target sequence corresponding to a sequence contained within SEQ ID NO:129 or 130, where the sense THS and antisense THS of the amplification oligomers of set (b) are each configured to specifically hybridize to a *Candida* sp. target sequence corresponding to a sequence contained within SEQ ID NO:131, and where the target-hybridizing sequences are selected such that the *Candida* sequence targeted by the antisense THS is situated downstream of the *Candida* sequence targeted by the sense THS (i.e., the at least two amplification oligomers are situated such that they flank the target region to be amplified). In some embodiments, the first *Candida* sp. target region corresponds to a region of SEQ ID NO:129 from about nucleotide position 133 or 161 to about nucleotide position 259, the second *Candida* sp. target region corresponds to a region of SEQ ID NO:130 from about nucleotide position 202 to about nucleotide position 308, and/or the third *Candida* sp. target region corresponds to a region of SEQ ID NO:131 from about nucleotide position 355 to about nucleotide position 554. In some variations, an oligomer combination includes (a) a first *Candida*-specific amplification oligomer comprising a first *Candida*-specific target hybridizing sequence substantially corresponding to the nucleotide sequence of residues 28-46 of SEQ ID NO:9. In some variations, an oligomer combination includes (a) a second *Candida*-specific amplification oligomer comprising a second *Candida*-specific target hybridizing sequence that is (i) a sequence of from 15 to 24 contiguous nucleotides contained in the sequence of SEQ ID NO:132 and that includes at least the sequence of SEQ ID NO:133, (ii) a sequence of from 20 to 23 contiguous nucleotides contained in the sequence of SEQ ID NO:152 and that includes at least the sequence of SEQ ID NO:151, or (iii) a sequence that substantially corresponds to the nucleotide sequence of SEQ ID NO:34. In some variations, an oligomer combination includes (b) a first *C. glabrata*-specific amplification oligomer comprising a first *C. glabrata*-specific target hybridizing sequence that is a sequence from 15 to 24 contiguous nucleotides contained in the sequence of SEQ ID NO:134 and that includes at least the sequence of SEQ ID NO:135. In some variations, an oligomer combination includes (b) a second *C. glabrata*-specific amplification oligomer comprising a second *C. glabrata*-specific target hybridizing sequence that is a sequence from 16 to 21 contiguous nucleotides contained in the sequence of SEQ ID NO:136 and that includes at least the sequence of SEQ ID NO:137.

In more specific embodiments of the present invention, an oligomer combination as above for determining the presence or absence of *Candida* sp. in a sample includes at least one of (A) an amplification oligomer comprising or consisting of the nucleotide sequence of residues 28-46 of SEQ ID NO:9, (B) an amplification oligomer comprising or consisting of the nucleotide sequence of SEQ ID NO:26, (C) an amplification oligomer comprising or consisting of the nucleotide sequence of residues 3-22 of SEQ ID NO:74, (D) an amplification oligomer comprising or consisting of the nucleotide sequence of SEQ ID NO:34, (E) an amplification oligomer comprising or consisting of the nucleotide sequence of residues 28-49 of SEQ ID NO:14, and (F) an amplification oligomer comprising or consisting of the nucleotide sequence of SEQ ID NO:12.

In certain embodiments, an amplification oligomer as described herein is a promoter primer or promoter provider further comprising a promoter sequence located 5' to the target-hybridizing sequence and which is non-complementary to the *Candida* sp. target nucleic acid. For example, in some embodiments of an oligomer combination as described herein for amplification of a *Candida* sp. target region, a first *Candida*-specific amplification oligomer as described above (e.g., a first *Candida*-specific amplification oligomer comprising a first *Candida*-specific target hybridizing sequence substantially corresponding to the nucleotide sequence of residues 28-46 of SEQ ID NO:9) and/or a first *C. glabrata*-specific amplification oligomer as described above (e.g., a first *C. glabrata*-specific amplification oligomer comprising a first *C. glabrata*-specific target hybridizing sequence that is a sequence from 15 to 24 contiguous nucleotides contained in the sequence of SEQ ID NO:134 and that includes at least the sequence of SEQ ID NO:135) is a promoter primer further comprising a 5' promoter sequence. In particular embodiments, the promoter sequence is a T7 RNA polymerase promoter sequence such as, for example, a T7 promoter sequence having the sequence shown in residues 1-27 of SEQ ID NO:9. In specific variations, a first *Candida*-specific amplification oligomer is a promoter primer having the sequence shown in SEQ ID NO:9 and/or a first *C. glabrata*-specific amplification oligomer is a promoter primer having the sequence shown in SEQ ID NO:14.

In some embodiments, an oligomer combination as described herein further includes a terminating oligonucleotide (also referred to herein as a "blocker" oligonucleotide) comprising comprises a base sequence substantially complementary (e.g., fully complementary) to a sequence contained within the target nucleic acid in the vicinity of the 5'-end of the target region. A terminating oligomer is typically used in combination with, e.g., a promoter provider amplification oligomer, such as, for example, in certain embodiments described herein relating to transcription-mediated amplification (TMA).

In some embodiments, an oligomer combination as described herein further comprises at least one *Candida*-specific capture probe oligomer and/or at least one *C. glabrata*-specific capture probe oligomer. In certain embodiments, a *Candida*-specific capture probe oligomer includes a target-hybridizing sequence substantially corresponding to a sequence contained in the complement of SEQ ID NO:129 or SEQ ID NO:30. In certain embodiments, a *C. glabrata*-specific capture probe oligomer includes a target-hybridizing sequence substantially corresponding to a sequence contained in the complement of SEQ ID NO:131. In some embodiments, a capture probe oligomer target-hybridizing sequence is covalently attached to a sequence or moiety that binds to an immobilized probe. In some embodiments, a *Candida*-specific capture probe oligomer has a target-hybridizing sequence that (i) is from 16 to 21 contiguous nucleotides contained in the sequence of SEQ ID NO:138 and includes at least the sequence of SEQ ID NO:139 or (ii) is from 15 to 25 contiguous nucleotides contained in the sequence of SEQ ID NO:140 and includes at least the sequence of SEQ ID NO:141. In some embodiments, a *C. glabrata*-specific capture probe oligomer has a target-hybridizing sequence that is from 16 to 27 contiguous nucleotides contained in the sequence of SEQ ID NO:142 and includes at least the sequence of SEQ ID NO:143 or SEQ ID NO:144. In particular embodiments, a *Candida*-specific capture probe target-hybridizing sequence comprises or consists of a nucleotide sequence selected from (i) the nucleotide sequence of residues 1-20 of SEQ ID NO:24 and (ii) the nucleotide sequence of residues 1-17 of SEQ ID NO:66; and/or a *C. glabrata*-specific capture probe target-hybridizing sequence comprises or consists of the nucleotide sequence of residues 1-26 of SEQ ID NO:48. In more specific variations, a *Candida*-specific capture probe oligomer has a nucleotide sequence selected from SEQ ID NO:24 and SEQ ID NO:66; and/or a *C. glabrata*-specific capture probe oligomer has the nucleotide sequence of SEQ ID NO:48. An oligomer combination may include at least two (e.g., three) capture probe oligomers as above. In some embodiments, an oligomer combination includes both a *Candida*-specific capture probe oligomer and a *C. glabrata*-specific capture probe oligomer as above; in some such embodiments, the oligomer combination further includes first and second *Candida*-specific capture probe oligomers, where each of the first and second *Candida*-specific capture probe oligomers is a *Candida*-specific capture probe oligomer as above. In certain embodiments, a capture probe oligomer is provided within a target capture reaction mixture.

In certain variations, an oligomer combination as described herein further comprises at least one detection probe oligomer configured to specifically hybridize to a *Candida* sp. target sequence that is amplifiable using first and second amplification oligomers targeting a *Candida* sp. target region (e.g., a *Candida* sp. target region that is flanked by the target-hybridizing sequences of first and second *Candida*-specific or *C. glabrata*-specific amplification oligomers as described herein). In some embodiments, the oligomer combination includes a *Candida*-specific detection probe that specifically hybridizes to (a-i) a first *Candida* sp. target region corresponding to a region of SEQ ID NO:129 from about nucleotide position 133 or 161 to about nucleotide position 259, (a-ii) a second *Candida* sp. target region corresponding to a region of SEQ ID NO:130 from about nucleotide position 202 to about nucleotide position 308, or (a-iii) the full complement of (a-i) or (a-ii). In some embodiments, the oligomer combination includes a *C. glabrata*-specific detection probe that specifically hybridizes to (b-i) a third *Candida* sp. target region corresponding to a region of SEQ ID NO:131 from about nucleotide position 355 to about nucleotide position 554 or (b-ii) the full complement of (b-i). In some embodiments, a *Candida*-specific detection probe includes a *Candida*-specific detection probe target-hybridizing sequence of from 18 to 22 contiguous nucleotides contained in the sequence of SEQ ID NO:145 and that includes at least the sequence of SEQ ID NO:146, or a target-hybridizing sequence that is the full complement of the foregoing. In some embodiments, a *C. glabrata*-specific detection probe includes a *C. glabrata*-specific detection probe target-hybridizing sequence selected from (A) a sequence of from 17 to 23 contiguous nucleotides contained in the sequence of SEQ ID NO:147 and that includes at least the sequence of SEQ ID NO:148, (B) a sequence that substantially corresponds to the sequence of residues 1-17 of SEQ ID NO:18, (C) a sequence that substantially corresponds to the sequence of residues 1-20 of SEQ ID NO:21, and (D) the full complement of any one of (A)-(C). In more particular embodiments, a *Candida*-specific detection probe target-hybridizing sequence comprises or consists of the sequence of residues 1-22 of SEQ ID NO:27 or the full complement thereof; and/or the *C. glabrata*-specific detection probe target-hybridizing sequence comprises or consists of the sequence of residues 1-17 of SEQ ID NO:60, the sequence of residues 1-23 of SEQ ID NO:45, the sequence of residues 1-17 of SEQ ID NO:18, the sequence of residues 1-20 of SEQ ID NO:21, or the full complement of any of the foregoing. In specific variations of a *Candida*-specific detection probe, the probe has the sequence of SEQ ID NO:27 or the full complement thereof. In specific variations of a *C. glabrata*-specific detection probe, the probe has the sequence of SEQ ID NO:60, SEQ ID NO:45, SEQ ID NO:18, SEQ ID NO:21, or the full complement of any of the foregoing. Suitable detection probes further include DNA equivalents and DNA/RNA chimerics of any of the above. A detection probe oligomer may contain a 2'-methoxy backbone at one or more linkages in the nucleic acid backbone. In some variations, an oligomer combination includes at least two detection probe oligomers (e.g., both a *Candida*-specific and a *C. glabrata*-specific detection probe as described herein). In some embodiments, the at least one detection probe oligomer is provided in an amplicon detection reaction mixture.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. Nos. 5,118,801 and 5,312,728, supra). Methods for using such hairpin probes are well-known in the art.

In yet other embodiments, a detection probe is a linear oligomer that does not substantially form conformations held by intramolecular bonds. In specific variations, a linear detection probe oligomer includes a chemiluminescent compound as the label, preferably an acridinium ester (AE) compound.

Also provided by the present invention are detection probe oligomers and capture probe oligomers as described herein.

In another aspect, the present invention provides methods for determining the presence or absence of *Candida* sp. in a sample using an oligomer combination as described herein. Such a method generally includes (1) contacting the sample with at least one of a first amplification oligomer combination and a second oligomer combination, where (a) the first amplification oligomer combination includes first and second *Candida*-specific amplification oligomers for amplifying a first *Candida* sp. target region corresponding to a region of SEQ ID NO:129 or a second *Candida* sp. target region corresponding to a region of SEQ ID NO:130, and (b) the second amplification oligomer combination includes first and second *C. glabrata*-specific amplification oligomers for amplifying a third *Candida* sp. target region corresponding to a region of SEQ ID NO:131; (2) performing an in vitro nucleic acid amplification reaction, where any *Candida* sp. target nucleic acid, if present in the sample, is used as a template for generating one or more amplification products corresponding to at least one of the first, second, and third target regions; and (3) detecting the presence or absence of the one or more amplification products, thereby determining the presence or absence of *Candida* sp. in the sample. A detection method in accordance with the present invention typically further includes the step of obtaining the sample to be contacted with the at least two oligomers. In certain embodiments, "obtaining" a sample to be used in steps (1)-(3) includes, for example, receiving the sample at a testing facility or other location where one or more steps of the method are performed, and/or retrieving the sample from a location (e.g., from storage or other depository) within a facility where one or more steps of the method are performed.

In certain embodiments, the method further includes purifying a *Candida* sp. target nucleic acid from other components in the sample before the contacting step. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Candida* sp. nucleic acid and other sample components.

In some embodiments, a *Candida* sp. target nucleic is selectively separated from other sample components by specifically hybridizing the *Candida* sp. target nucleic acid to a capture probe oligomer. The capture probe oligomer comprises a target-hybridizing sequence configured to specifically hybridize to a *Candida* sp. target sequence so as to form a target-sequence:capture-probe complex that is separated from sample components. Suitable capture probe target-hybridizing sequences include sequences as described above with respect to *Candida*-specific capture probes and/or *C. glabrata*-specific capture probes that may be used in certain embodiments of oligomer combinations for detecting *Candida* sp. In a preferred variation, the specific target capture binds the *Candida* sp. target:capture-probe complex to an immobilized probe to form a target:capture-probeimmobilized-probe complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components. In some embodiments, a sample suspected of containing *Candida* sp. is contacted with both a *Candida*-specific capture probe oligomer and a *C. glabrata* capture probe oligomer; in some such embodiments, the sample is further contacted with a second *Candida*-specific capture probe oligomer.

In more specific embodiments, a capture probe oligomer includes a tail portion (e.g., a 3' tail) that is not complementary to the *Candida* sp. target sequence but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle. For example, in specific embodiments of a capture probe comprising a 3' tail, the capture probe has a sequence selected from SEQ ID NO:24, SEQ ID NO:66, and SEQ ID NO:48.

Target capture typically occurs in a solution phase mixture that contains one or more capture probe oligomers that hybridize specifically to a *Candida* sp. target sequence under hybridizing conditions, usually at a temperature higher than the $T_m$ of the tail-sequenceimmobilized-probe-sequence duplex. For embodiments comprising a capture probe tail, the *Candida* sp.-target:capture-probe complex is captured by adjusting the hybridization conditions so that the capture probe tail hybridizes to the immobilized probe, and the entire complex on the solid support is then separated from other sample components. The support with the attached immobilized-probe:capture-probe:*Candida*-sp.-target-sequence may be washed one or more times to further remove other sample components. Preferred embodiments use a particulate solid support, such as paramagnetic beads, so that particles with the attached *Candida*-sp.-target:capture-probeimmobilized-probe complex may be suspended in a washing solution and retrieved from the washing solution, preferably by using magnetic attraction. To limit the number of handling steps, a *Candida* sp. target nucleic acid may be amplified by simply mixing the *Candida* sp. target sequence in the complex on the support with amplification oligomers and proceeding with amplification steps.

Amplifying a *Candida* sp. target sequence utilizes an in vitro amplification reaction using at least two amplification oligomers that flank a target region to be amplified. In some embodiments, a target region to be amplified corresponds to a region of SEQ ID NO:129 from about nucleotide position 133 or 161 to about nucleotide position 259. In some embodiments, a target region to be amplified corresponds to a region of SEQ ID NO:130 from about nucleotide position 202 to about nucleotide position 308. In some embodiments, a target region to be amplified corresponds to a region of SEQ ID NO:131 from about nucleotide position 355 to about nucleotide position 554. Particularly suitable amplification oligomer combinations for amplification of these target regions are described herein. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art and are readily used in accordance with the methods of the present invention.

For example, some amplification methods that use TMA amplification include the following steps. Briefly, the target nucleic acid that contains the sequence to be amplified is provided as single-stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

Detection of the amplified products may be accomplished by a variety of methods. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. In particular, the amplified product will contain a target sequence in or complementary to a sequence in a *Candida* sp. RPR1 gene or RNA encoded by the RPR1 gene, and a probe will bind directly or indirectly to a sequence contained in the amplified product to indicate the presence of *Candida* sp. nucleic acid in the tested sample.

Preferred embodiments of detection probes that hybridize to the complementary amplified sequences may be DNA or RNA oligomers, or oligomers that contain a combination of DNA and RNA nucleotides (also referred to herein as an "RNA/DNA chimeric"), or oligomers synthesized with a modified backbone, e.g., an oligomer that includes one or more 2'-methoxy substituted ribonucleotides. Probes used for detection of the amplified *Candida* sp. sequences may be unlabeled and detected indirectly (e.g., by binding of another binding partner to a moiety on the probe) or may be labeled with a variety of detectable labels. Particular embodiments of detection probes suitable for use in accordance with methods of the present invention are further described herein. In some embodiments of the method for detecting *Candida* sp. sequences, such as in certain embodiments using transcription-mediated amplification (TMA), the detection probe is a linear chemiluminescently labeled probe, more preferably, a linear acridinium ester (AE) labeled probe. In other embodiments, the detection probe comprises both a fluorescent label and a quencher (e.g., a molecular torch or a molecular beacon).

Oligomers that are not intended to be extended by a nucleic acid polymerase preferably include a blocker group that replaces the 3' OH to prevent enzyme-mediated extension of the oligomer in an amplification reaction. For example, blocked amplification oligomers and/or detection probes present during amplification preferably do not have a functional 3' OH and instead include one or more blocking groups located at or near the 3' end. A blocking group near the 3' end is preferably within five residues of the 3' end and is sufficiently large to limit binding of a polymerase to the oligomer, and other preferred embodiments contain a blocking group covalently attached to the 3' terminus. Many different chemical groups may be used to block the 3' end, e.g., alkyl groups, non-nucleotide linkers, alkane-diol dideoxynucleotide residues, and cordycepin.

Examples of oligomers that are typically blocked at the 3' end—and which are particularly suitable in certain embodiments using transcription-mediated amplification—are promoter providers. As described previously, a promoter provider comprises first target-hybridizing region and, situated 5' to the first region, a second region comprising a promoter sequence for an RNA polymerase. The promoter provider oligonucleotide is modified to prevent the initiation of DNA synthesis from its 3'-terminus, such as by including a blocker group as discussed above.

Another example of typically 3'-blocked oligomers are terminating ("blocker") oligonucleotides, previously described above. A terminating oligomer is typically used in combination with, e.g., a promoter provider amplification oligomer, such as, for example, in certain embodiments described herein relating to transcription-mediated amplification (TMA). A terminating oligomer hybridizes to a sequence contained within the target nucleic acid in the vicinity of the 5'-end of the target region so as to "terminate" primer extension of a nascent nucleic acid that includes a priming oligonucleotide, thereby providing a defined 3'-end for the nascent nucleic acid strand.

Other embodiments using transcription-mediated amplification utilize a promoter primer, which comprises a first target-hybridizing region and, situated 5' to the first region, a second region comprising a promoter sequence for an RNA polymerase, but which is not modified to prevent the initiation of DNA synthesis from its 3'-terminus. In some embodiments, a promoter primer for use in accordance with the detection method comprises (i) a *Candida*-specific target-hybridizing sequence substantially corresponding to the nucleotide sequence of residues 28-46 of SEQ ID NO:9 or (ii) a *C. glabrata*-specific target-hybridizing sequence from 15 to 24 contiguous nucleotides contained in the sequence of SEQ ID NO:134 and that includes at least the sequence of SEQ ID NO:135. In some such embodiments, the promoter primer comprises (i) a *Candida*-specific target-hybridizing sequence comprising or consisting of the nucleotide sequence of residues 28-46 of SEQ ID NO:9 or (ii) a *C. glabrata*-specific target-hybridizing sequence comprising or consisting of the nucleotide sequence of residues 28-49 of SEQ ID NO:14. In more specific variations, a promoter primer for use in accordance with the detection method has the sequence shown in SEQ ID NO:9 or SEQ ID NO:14.

Assays for detection of a *Candida* sp. nucleic acid may optionally include a non-*Candida* sp. internal control (IC) nucleic acid that is amplified and detected in the same assay reaction mixtures by using amplification and detection oligomers specific for the IC sequence. IC nucleic acid sequences can be RNA template sequences (e.g., and in vitro transcript), synthetic nucleic acid sequences that are spiked into a sample or the IC nucleic acid sequences may be a cellular component. IC nucleic acid sequences that are cellular components can be from exogenous cellular sources or endogenous cellular sources relative to the specimen. In these instances, an internal control nucleic acid is co-amplified with the *Candida* sp. nucleic acid in the amplification reaction mixtures. The internal control amplification product and the *Candida* sp. target sequence amplification product can be detected independently.

Also provided by the subject invention is a reaction mixture for determining the presence or absence of a *Candida* sp. target nucleic acid in a sample. A reaction mixture in accordance with the present invention at least comprises one or more of the following: an oligomer combination as described herein for amplification of a *Candida* sp. target nucleic acid; a capture probe oligomer as described herein for purifying the *Candida* sp. target nucleic acid; and a detection probe oligomer as described herein for determining the presence or absence of a *Candida* sp. amplification product. The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a *Candida* sp. target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: an amplification oligomer combination as described herein for amplification of a *Candida* sp. target nucleic acid; a capture probe oligomer as described herein for purifying the *Candida* sp. target nucleic acid; and a detection probe oligomer as described herein for determining the presence or absence of a *Candida* sp. amplification product. The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). Oligomers as described herein may be packaged in a variety of different embodiments, and those skilled in the art will appreciate that the invention embraces many different kit configurations. For example, a kit may include amplification oligomers for only one target region of a *Candida* sp. genome, or it may include amplification oligomers for multiple *Candida* sp. target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). In certain embodiments, the kit further includes a set of instructions for practicing methods in accordance with the present invention, where the instructions may be associated with a package insert and/or the packaging of the kit or the components thereof.

The invention is further illustrated by the following non-limiting examples.

Example 1: Exemplary Protocol for Performing *Candida* Amplification and Detection Assays One exemplary protocol for performing *Candida* amplification and detection reactions is as follows: (a) Prepare reagents. The total volume of each component was determined based on the anticipated number of tests to be performed. Also the needed volume was calculated for each oligo stock material to add to each reagent mix to yield the desired final oligonucleotide concentrations. (1) A total of 4 separate reagents was then prepared: TCR (Target Capture Reagent: poly-T magnetic beads (magnetic beads joined to adT.sub.14 oligonucleotide), target capture oligos, and (optionally) T7 primers in an aqueous HEPES buffer), AMP (Amplification Reagent: NT7 primers in a TRIS buffered solution containing salts and nucleotides), PRO (Promoter Reagent: T7 and torch oligos in a TRIS buffered solution containing salts and nucleotides), and ENZ (Enzyme Solution: a mixture of MMLV reverse transcriptase and T7 RNA polymerase in an aqueous buffer with glycerol). For the current examples, unless stated otherwise, the following concentrations of oligonucleotides were used: 5 pmol/reaction each T7 oligo in the TCR, 15 pmol/reaction each target capture oligo (TCO) in the TCR, 15 pmol/reaction each non-T7 oligo in the AMP, 15 pmol/reaction each T7 oligo in the PRO, and 15 pmol/reaction each torch oligo in the PRO. In preparing each reagent, a volume of the oligomerless version of the reagent was determined based upon the volume of oligonucleotides to add to the reagent. Then, the oligomerless reagent was aliquoted and each aliquot was brought up to full volume using the calculated oligomer volumes.

Reaction were performed on an automated system (e.g., the Panther system (Hologic, Inc., Marlborough, MA)), in a pure system or in a semi-manual method. For reactions run on an automated system such as the Panther system, prepared reagents (TCR, AMP, PRO, ENZ) were loaded into the automated device followed by the samples. The automated system then performed the Target Capture, amplification, and data collection. For reactions run in a "pure system" there was not a target capture step. Rather, target nucleic acids (e.g., an in vitro transcript) was added directly to the AMP mix in a microtiter plate, then proceed to amplification reactions. For the semi-manual reactions, the target capture and wash steps were performed as follows:

If running with a semi-manual method, perform target capture and wash steps as follows: (1) AMP mix was aliquoted at 50 uL/well to a 96-well PCR plate. Aptima Wash Buffer (e.g., wash solution (Hologic, Inc., Marlborough, MA, Cat. No. 302179)) was aliquoted at 500 uL/well to a round bottom Kingfisher deep-well plate, and at 200 uL/well to a shallow Kingfisher 96-well plate. These 3 plates were then set aside. (2) TCR was aliquoted at 100 uL/well into a deep well plate, followed by 400 uL sample/well. This sample containing plate was then covered, placed on the Torrey Pines heat block (Torrey Pines Scientific, CA, Cat. No. IC25), and incubated at 62 degrees Celsius for 30 minutes. The heated plate was allowed to slowly cool to room temperature (20 minutes). (3) The room temperature plate was then moved to the Kingfisher instrument for bead washing as generally described in the package insert for the Aptima HCV RNA qualitative assay (Hologic, Inc., Cat. No. 302179). A tip comb (magnet cover) was placed on the plate, the plate was placed on the Kingfisher instrument, and a wash program was executed to collects the beads, transfer collected beads to the deep-well wash plate, mix the plate, re-capture the beads and transfer them to the shallow-well wash plate. (4) Following the wash program, the bead-containing plate was transferred to a Kingfisher instrument with a smaller comb (magnet cover), the washed beads were then collected, and transferred to/released into the plate containing AMP reagent.

Amplification and detection reactions were generally performed as follows: The plate containing AMP reagent and samples was covered and incubated at 44 degrees Celsius for about 5 minutes using a Thermomixer® (shaker/heat block) (Eppendorf, Hamburg DE, Eppendorf Model 5355). After the 5 minute incubation, 25 uL of Enzyme Mix was added to each well and the plate was again covered. The covered plate was mixed for 1 minute at 1400 rpm, then incubated for 5 minutes at 44 degrees Celsius. Following this incubation 25 uL of Promoter Mix (PRO) was added to each well and the plate was mixed for 1 minute at 1400 rpm. The plate was then covered with an optical plate seal and the sealed plate was then immediately placed on the Stratagene realtime cycler (Model Mx3005p, Agilent Technologies, CA) and incubated at 43 degrees Celsius. Data was collected from each of the FAM, HEX and ROX channels for 150 cycles of 30 seconds each. Data was exported and analyzed.

Example 2: *Candida* RT-TMA Oligo Screening

This Example illustrates an assay for the amplification and detection of *Candida* species *albicans, parapsilosis, tropicalis, and dubliniensis*, and for the separate amplification and detection of *Candida glabrata.*

The assay consists of two sets of amplification and detection systems. The first system consists of a single broad-range T7 oligo, a pair of non-T7 oligos, and a labeled torch oligo for the amplification and detection of *C. albicans, C. parapsilosis, C. tropicalis*, and *C. dubliniensis*. The second system consists of a T7, non-T7, and a labeled torch oligo specific for the amplification and detection of *C. glabrata*. The assay includes three target capture oligos (TCO), with one TCO specific to *C. glabrata* while the other two TCOs capture species detected by the broad-range amplification system. All oligos of a Broad Range oligo combination and a *C. glabrata* specific oligo combination are listed in Table 1. Oligomer sequences evaluated in this study are shown in Table 2. The full amplification system can be run in a Bi-Phasic real-time TMA assay format using separate promoter and amplification reagents. The full amplification Bi-Phasic system involves 4 main steps: (i) Target Capture of a Target Nucleic Acid in a Sample: The target capture reaction included the general steps of mixing a target nucleic acid with a target capture oligomer (TCO), a poly-T magnetic bead, and a T7 promoter primer (T7). The TCO and the T7 were hybridized to the target nucleic acid, and also hybridizing the 3' end of the TCO to the immobilized probe of the poly-T magnetic bead. The resulting hybridization complex was then separated from other components of the sample. (ii) The separated hybridization complex was washed to remove any interfering substances, unbound targets and T7s remining in the sample, resulting in a substantially purified hybridization complex. (iii) An initial linear amplification was then performed. The substantially purified hybridization complex was resuspended in a linear amplification reagent containing a non-T7 primer (NT7) and the necessary reagents for amplification (i.e., reverse transcriptase with RNase activity, dNTPs, and salts). Absent from the linear amplification reagent were any additional T7 amplification oligomers. As a result, the linear amplification reaction produced an initial amount of RNA transcript as amplicons. (iv) An exponential amplification of the linear amplification products was then performed. Briefly, after a duration of time in the linear amplification reaction, an exponential amplification reagent was added to the reaction. The exponential amplification reagent contained T7 amplification oligomers and torch detection probe oligomers. The exponential amplification regent thus provided the reaction components necessary for producing double stranded DNA products (with a double stranded promoter sequence) from RNA transcript amplicons, thus exponentially increasing the number of double stranded DNA molecules producing RNA transcript amplicons. As the RNA transcript amplicons are generated, torches bound the amplicons to generate detection signal.

TABLE 1

Oligonucleotides for *Candida* RNA Real-time TMA Assay System

| Amplification Type | Target[1] | TCO | T7 | nT7 | Torch |
|---|---|---|---|---|---|
| Broad Range | *C. albicans*<br>*C. parapsilosis*<br>*C. dubliniensis*<br>*C. tropicalis* | SEQ ID NO: 24<br>SEQ ID NO: 66 | SEQ ID NO: 9 | SEQ ID NO: 26<br>SEQ ID NO: 34 | SEQ ID NO: 27 |
| *Glabrata* | *C. glabrata* | SEQ ID NO: 48 | SEQ ID NO: 14 | SEQ ID NO: 12 | SEQ ID NO: 60 |

[1]Target nucleic acid in this example was an in vitro transcript.

TABLE 2

Oligomer Sequences

| Oligomer Type | SEQ ID NO: | Sequence (5' to 3') |
|---|---|---|
| TCO | 24 | AGATCGGTATCGGGTGCTTGTTTAAAAAAAAAA AAAAAAAAAAAAAAAAAAAA |
| TCO | 66 | GATGGAGCGTACCACCGTTTAAAAAAAAAAAAA AAAAAAAAAAAAAAAAA |
| TCO | 48 | GCTCAGAAAACCAGAAGCGAAACGGGTTTAAAA AAAAAAAAAAAAAAAAAAAAAAAAA |
| T7 | 10 | AATTTAATACGACTCACTATAGGGAGATGATCG GTATCGGGTGCTTG |
| T7 | 9 | AATTTAATACGACTCACTATAGGGAGATCAAGT TCGCATATTGCAC |
| T7 | 14 | AATTTAATACGACTCACTATAGGGAGAATACTG GACCGACATCCTTACG |
| nT7 | 153 | GTGAAAGCGCATGGGC |
| nT7 | 154 | GAAATCTTCAGAGCCCGAAGG |
| nT7 | 7 | GAAATTCGGTGGTACGCTCCAT |
| nT7 | 26 | CGTTACAAGAAATATACACGG |
| nT7 | 34 | GGTAGTTTGGCTTTTCTTTGG |
| nT7 | 12 | GCATTGGAGTTTCTGCTG |

TABLE 2-continued

| Oligomer Sequences | | |
|---|---|---|
| Oligomer Type | SEQ ID NO: | Sequence (5' to 3') |
| nT7 | 6 | GTGGGAAATTCGGTGGTA |
| nT7 | 73 | CTTCCTTAGCGTGAAAACGCA |
| nT7 | 74 | AGGCTGTAAAAGGTCTGCTTCGT |
| nT7 | 75 | AGAAATCTTCAGAGCCCGA |
| Torch | 27 | GGAAUGGCGCCGUGGAUGGUUGCAUUGG |
| Torch | 60 | GGAUGUGACUGUCAUGCCAUCC |
| Torch | 28 | GCCGUCAGCCAACCAUCCACGGC |
| Torch | 4 | AUGGGAAUGGCGCCGUGGAUGGUCCCAU |
| Torch | 18 | GGUGGAUUUGUGCGACACCACC |
| Torch | 45 | CAUGCGCUUUUCUGAGAAGCAACGCAUG |
| Torch | 46 | CUGAGAAGCAACUUCUCUAUUAACGCUCAG |
| Torch | 21 | GGCAGAGACGUAUGGGCCUGCUGCC |
| Torch | 3 | CCAAGUCCUUGUGGCUUGGCCUUGG |
| Torch | 155 | GGAAUGGCGCCGUGGAUGGUUGCAUUCC |

Oligo Selection Summary

The selection of oligos was primarily based on the following criteria:

1. Signal to noise ratio of fluorescence torch
2. Appearance of amplification curve (if any); sigmoidal curves usually indicate efficient amplification
3. TTime
4. Limit of detection For simplicity, only limit of detection (sensitivity) results are shown in this Example. Only the lowest concentration tested, in in vitro transcript copies per reaction, is shown in each table.

Amplification and detection was performed in a pure amplification system. The pure amplification system doesn't involve target capture, wash, or biphasic amplification. Instead, all amplification oligos and an in vitro transcript target nucleic acid are added to one common amplification reagent and after an incubation period, the enzyme is added with the torch for real time detection. Oligo screening was performed in a pure system for simplification purposes. Unless specified otherwise in this Example, most of the screening process was performed using the pure amplification system.

Broad Range System

T7 SEQ ID NO:9 and SEQ ID NO:10 were each tested along with various combinations of non-T7 oligos, torches. Initial testing was done using only a *C. albicans* in vitro transcript as target nucleic acid (serially diluted). Table 3 shows the oligo combinations that were screened and the sensitivity results. The lowest concentration of in vitro transcript (IVT) tested was 1E4.

TABLE 3

| T7 Oligo Screening for Broad Range System | | | |
|---|---|---|---|
| T7 Oligo | Non-T7 Oligo | Torch | Sensitivity for *C. albicans* IVT copies per reaction |
| SEQ ID NO: 9 | SEQ ID NO: 12 | SEQ ID NO: 4 | 1E6 |
| SEQ ID NO: 9 | SEQ ID NO: 7 | SEQ ID NO: 4 | 1E6 |
| SEQ ID NO: 10 | SEQ ID NO: 12 | SEQ ID NO: 4 | 1E6 |
| SEQ ID NO: 10 | SEQ ID NO: 7 | SEQ ID NO: 4 | 1E6 |

All oligo combinations showed the same limit of detection (1E6), but the combination of SEQ ID NO:9 (T7) with SEQ ID NO:12 (non-T7) showed slightly faster TTimes in this experiment. Changes in oligo concentrations did not significantly change the sensitivities for these oligonucleotide combinations. All future tests were performed using a T7 oligomer with the sequence shown in SEQ ID NO:9.

A new combination of oligos was then tested to address the low RFU signal in *C. parapsilosis* and to try to improve the sensitivity of all *Candida* species targeted in this system. Table 4 shows the oligos tested in this screening. In the original screening, other strains of *Candida*, except, *C. parapsilosis*, showed amplification similar to *C. albicans*. Thus, these oligo combinations were tested with *C. albicans* and *C. parapsilosis*.

TABLE 4

| Non-T7 and Torch Screening | | | | |
|---|---|---|---|---|
| T7 Oligo | non-T7 Oligo | Torch | Sensitivity for *C. albicans* in IVT copies per reaction | Sensitivity for *C. parapsilosis* in IVT copies per reaction |
| SEQ ID NO: 9 | SEQ ID NO: 153 | SEQ ID NO: 27 | 1E4 | 1E6 |
| SEQ ID NO: 9 | SEQ ID NO: 153 | SEQ ID NO: 28 | 0 | 0 |
| SEQ ID NO: 9 | SEQ ID NO: 26 | SEQ ID NO: 27 | 1E7 | 0 |
| SEQ ID NO: 9 | SEQ ID NO: 26 | SEQ ID NO: 28 | 0 | 0 |

Oligo combination of SEQ ID NO:9, SEQ ID NO:26 and SEQ ID NO:27 significantly improved the sensitivity for *C. albicans* but no amplification was obtained for *C. parapsilosis* at the concentrations tested. Weak amplification of *C. parapsilosis* was observed at 1E8 IVT copies per reaction. Other *Candida* strains were tested with the oligo combination of SEQ ID NO:9, SEQ ID NO:26 and SEQ ID NO:27. Results are shown in Table 5.

TABLE 5

Sensitivity of *C. albicans*, *C. dubliniensis*, and *C. tropicalis* with New Set of Broad Range Oligos

| T7 Oligo | Non-T7 Oligo | Torch | Sensitivity (IVT copies/rxn) *C. albicans* | *C. dubliniensis* | *C. tropicalis* |
|---|---|---|---|---|---|
| SEQ ID NO: 9 | SEQ ID NO: 26 | SEQ ID NO: 27 | 1E1 | 1E1 | 1E2 |

As noted above, amplification of *C. parapsilosis* as well as the other *Candida* species was seen using SEQ ID NO:9, SEQ ID NO:12 and SEQ ID NO:4. In a further assay, SEQ ID NO:9, and SEQ ID NO:4 or SEQ ID NO:27 were tested in combination with a number of non-T7 oligos to determine sensitivity of amplification and detection of *C. parapsilosis*. Table 6 shows complete set of oligos used. The lowest tested concentration of IVT copies/reaction was 1E4/uL.

TABLE 6

*C. parapsilosis* sensitivity with SEQ ID NO: 27, SEQ ID NO: 9, and SEQ ID NO: 6

| T7 Oligo | Non-T7 Oligo | Torch | Sensitivity for *C. parapsilosis* (IVT/reaction) |
|---|---|---|---|
| SEQ ID NO: 9 | SEQ ID NO: 12 | SEQ ID NO: 4 | 1E6 |
| SEQ ID NO: 9 | SEQ ID NO: 12 | SEQ ID NO: 27 | 1E8 |
| SEQ ID NO: 9 | SEQ ID NO: 154 | SEQ ID NO: 4 | 0 |
| SEQ ID NO: 9 | SEQ ID NO: 154 | SEQ ID NO: 27 | 0 |
| SEQ ID NO: 9 | SEQ ID NO: 34 | SEQ ID NO: 4 | 1E4 |
| SEQ ID NO: 9 | SEQ ID NO: 34 | SEQ ID NO: 27 | 1E4 |

The oligo combination SEQ ID NO:9, SEQ ID NO:26 and SEQ ID NO:34, and SEQ ID NO:27 were then tested with the Bi-Phasic amplification approach on an automated amplification and detection system (Panther system, Hologic, Inc.). When the pure system and Bi-Phasic system results where compared, no significant decrease in sensitivity was observed for any of the *Candida* species except for *C. dubliniesis.*

Combining both non-T7 oligos in one single reaction using the Bi-Phasic system did not affect the amplification of any of the targets when compared to Bi-Phasic reactions that used the same two nonT7 oligos (SEQ ID NO:26 and SEQ ID NO:34) in individual reactions (see Tables 4, 5, and 6 for results with oligos in individual reactions). Pure system vs Bi-Phasic system results are shown on Table 7 below. Sensitivity concentrations are in IVT copies/rxn.

TABLE 7

Sensitivity of *Candida* system in the Bi-Phasic assay compared to the pure system

| System | T7 (SEQ ID NO) | Non-T7 (SEQ ID NO) | Torch (SEQ ID NO) | Sensitivity *C. albicans* | *C. tropicalis* | *C. dubliniensis* | *C. parapsilosis* |
|---|---|---|---|---|---|---|---|
| Bi-phasic | 9 | 26 & 34 | 27 | 1E1 | 1E2 | 1E2 | 1E1 |
| Bi-phasic | 9 | 26 | 27 | 1E1 | 1E2 | 1E2 | 0 |
| Bi-phasic | 9 | 34 | 27 | 0 | 0 | 0 | 1E3 |
| Pure | 9 | 26 | 27 | 1E1 | 1E2 | 1E1 | 0 |
| Pure | 9 | 34 | 27 | 0 | 0 | 0 | 1E4[2] |

[2]Lowest concentration tested for *C. parapsilosis* in the pure system.

*C. parapsilosis* amplification and detection sensitivity was 1E8 IVT copies/reaction when using SEQ ID NO:27 with SEQ ID NO:9 and SEQ ID NO:12. Substituting the torch SEQ ID NO:27 with the torch SEQ ID NO:4 showed a sensitivity of 1E6 IVT copies/rxn. A significantly improved sensitivity was seen for both of torch SEQ ID Nos:4 & 27 when the non-T7 primers SEQ ID NO:12 was substituted with non-T7 primer SEQ ID NO:34.

*C. albicans* was tested using SEQ ID NO:9, SEQ ID NO:34 and, separately, each of SEQ ID Nos:4 & 27. In these assays amplification and detection of *C. albicans* was absent. However, by adding the non-T7 primer SEQ ID NO:26 into these reactions, amplification and detection of all *Candida* species, including *C. parapsilosis*, was observed. However, the *C. albicans* amplification efficiency was negatively affected with Ttime delays at the low IVT copy levels and a 1 log decrease (from 1E4 to 1E5) in the limit of detection.

Example 3: Sensitivity Testing of a Feasibility RT-TMA Reagent Formulation for Amplification and Detection of *Candida albicans, Candida dubliniensis, Candida parapsilosis, Candida tropicalis*, and *Candida glabrata*

Analytical sensitivity was evaluated using lysates from each of five species of *Candida*. Each lysate was generated by growing the organism in culture, quantitating by plate count, and diluting in sample transport medium (STM) (e.g., Cary-Blair Transport Medium (Becton-Dickenson & Co., NJ, Cat. No. 211102); and e.g., Aptima Vaginal Swab Specimen Collection Kits (Hologic, Inc., Marlborough, MA, Cat. No. 301162)) to a normalized concentration in colony forming units per milliliter (CFU/mL). Lysates in STM were serially diluted in STM to final concentrations of 100, 300, 1000, 3000, 10000, and 30000 CFU/mL.

Fifteen replicates of each concentration were used as samples in a real time transcription mediated amplification and detection reaction (RT-TMA) on an automated amplification and detection system (the Panther system (Hologic, Inc.)). The formulation was configured to amplify and detect a nucleic acid internal control as well as the RNAse P RNA from each of the following *Candida* species: *C. albicans, C. dubliniensis, C. parapsilosis*, and *C. tropicalis* (collectively referred to as "Broad Range"), and *C. glabrata*. The Broad Range targets were amplified with a single T7 and two non-T7 primers and then detected with a single probe configured as a torch. *C. glabrata* was amplified with a single T7, a single non-T7 and a single torch oligo differently labeled from the Broad Range torch oligo so to distinguish Broad Range from *C. glabrata*. An internal control target along with amplification and detection oligos (not shown) was included, and the detection oligo was differently labeled so to be distinguishable from targets. The nucleotide sequences of the *Candida* oligos used in the triplex reaction are shown in Table 8 below.

TABLE 8

| SEQ ID NO: | Amp Type | Sequence | Type |
|---|---|---|---|
| 12 | *Glabrata* | GCATTGGAGTTTCTGCTG | NT7 |
| 34 | Broad Range | GGTAGTTTGGCTTTTCTTTGG | NT7 |
| 26 | Broad Range | CGTTACAAGAAATATACACGG | NT7 |
| 14 | *Glabrata* | AATTTAATACGACTCACTATAGGGAGAATACTGGACCGACATCCTTACG | T7 |
| 9 | Broad Range | AATTTAATACGACTCACTATAGGGAGATCAAGTTCGCATATTGCAC | T7 |
| 48 | *Glabrata* | GCTCAGAAAACCAGAAGCGAAACGGGTTTAAAAAAAAAAAAAAAAAAAAAAAAAAAAAA | TCO |
| 24 | Broad Range | AGATCGGTATCGGGTGCTTGTTTAAAAAAAAAAAAAAAAAAAAAAAAAAAAAAA | TCO |
| 66 | Broad Range | GATGGAGCGTACCACCGTTTAAAAAAAAAAAAAAAAAAAAAAAAAAAAAAAA | TCO |
| 27 | Broad Range | GGAAUGGCGCCGUGGAUGGUUGCAUUGG | torch |
| 60 | *Glabrata* | GGAUGUGACUGUCAUGCCAUCC | torch |

Results: Positivity was estimated as RFU's above a threshold at various cutoff times (in minutes). Table 9 below shows the numbers of positive replicates out of 15 using an RFU threshold of 3000 and a T-time cutoff of 20 minutes for Broad Range *Candida* species and an RFU threshold of 1600 and a T-time cutoff of 25 minutes for *Candida glabrata*.

TABLE 9

| | Target Level (CFU/mL) | | | | | | |
|---|---|---|---|---|---|---|---|
| Target species | 0 | 100 | 300 | 1000 | 3000 | 10000 | 30000 |
| *C. albicans* | 0 | 0 | 2 | 14 | 15 | 15 | 15 |
| *C. parapsilosis* | 0 | 0 | 11 | 15 | 15 | 15 | 15 |
| *C. glabrata* | 0 | 0 | 0 | 0 | 14 | 15 | 15 |
| *C. dubliniensis* | 0 | 0 | 0 | 0 | 3 | 15 | 15 |
| *C. tropicalis* | 0 | 1 | 14 | 15 | 15 | 15 | 15 |

A Probit analysis was performed to estimate the 95% and 50% detection levels for each analyte. For *C. albicans*, C50 (estimated level with 50% probability of positivity) was 583 CFU/mL, with 95% confidence limits of 383-747, and the C95 (estimated level with a 95% probability of positivity) was 1035 CFU/mL, with 95% confidence limits of 809-1563. For *C. tropicalis*, the C50 was 200 (124-244) and the C95 was 309 (253-437). For *C. dubliniensis*, the C50 was 3142 (3000-3292) and the C95 was 3337 (3195-3495). For *C. parapsilosis* the C50 was 292 (285-300) and the C95 was 310 (302-319). For *C. glabrata* the C50 was 2841 (2763-2922) and the C95 was 3012 (2929-3097) CFU/mL.

Example 4: Specificity and Interference Testing of Oligonucleotides for Amplification and Detection of *Candida albicans, Candida dubliniensis, Candida parapsilosis, Candida tropicalis*, and *Candida glabrata*

In order to test the specificity of the reagent formulation from Example 3, a panel of non-targeted organisms was built in STM. Each panel member consisted of cellular lysate material from one to five non-targeted organisms diluted in STM to a final concentration of one-million CFU/mL. Organisms for which this concentration was not feasible (*Trichomonas vaginalis, Chlamydia trachomatis*) were tested at a lower concentration (43000 and 38500 organisms per mL, respectively). The organisms in each sample panel are as follows. Panel 1: *Acinetobacter iwoffii, Actinomyces israelii, Alcaligenes faecalis, Bacteroides fragilis*. Panel 2: *Clostridium difficile, Corynebacterium genitalium, Enterobacter cloacae, Enterococcus feacalis, Escherichia coli*. Panel 3: *Bifidobacterium adolescentis, Campylobacter jejuni, Fusobacterium nucleatum, Haemophilus ducreyi, Klebsiella pneumoniae*. Panel 4: *Listeria monocytogenes, Mycoplasma hominis, Peptostreptococcus magnus, Propionibacterium acnes*. Panel 5: *Neisseria gonorrhoeae, Trichomonas vaginalis, Ureaplasma urealyticum, Ureaplasma Parvum*. Panel 6: *Candida krusei, Candida lusitaniae, Prevotella bivia, Eggerthella lenta*. Panel 10: *Pseudomonas aeruginosa, Mobiluncus curtisii, Chlamydia trachomatis, Cryptococcus neoformans*. Panel 11: *Staphylococcus aureus, Staphylococcus epidermidis, Streptococcus agalactiae, Streptococcus pyogenes*. Panel 12: *Leptotrichia bucalis, Proteus vulgaris, Megaspahaera elsdenii, Atopobium vaginae*. Panel 13: *Lactobacillus acidophilus, Lactobacillus mucosae, Lactobacillus gastricus, Lactobacillus iners*. Panel 14: *Lactobacillus crispatus, Lactobacillus jensenii, Lactobacillus gasseri*. Panel 15: *Gardnerella vaginalis*. Ten replicate reactions of each panel were run on the automated Panther system with Broad Range and *C. glabrata* oligonucleotide combinations as shown in Table 1.

Specificity results: No reactions showed positivity as determined by RFU ranges above a threshold of 1600 in the fluorescence channel used for *C. glabrata* detection or a threshold of 3000 for the fluorescence channel used for detection of the Broad Range oligo combination. All replicates of the internal control were positive, with RFU ranges exceeding a threshold of 1600.

In order to determine if detection of *Candida* organisms would be impaired by the presence of non-targeted organisms in a sample, the specificity panels described above were each spiked with target organisms before being run on the automated Panther system with the Broad Range and *C. glabrata* oligonucleotide combinations shown in Table 1. Panels were spiked to either 3000 CFU/mL of *C. parapsilosis* or to 3000 CFU/mL of *C. albicans* and 3000 CFU/mL *C. glabrata*. Results: all of the reactions (10 replicates per condition) were positive as determined by RFU range. No significant inhibition was observed.

Example 5: Evaluation of Alternate Torch Designs for Detection of *Candida glabrata*

Six alternate torch probe designs were directly compared for detection of *Candida* glabrata in a Bi-phasic amplification and detection format. Each torch was labeled with a FAM fluorophore and a Dabcyl quencher. Each reaction was 10000 CFU/reaction of *Candida glabrata* lysate diluted in STM. Negative control was STM without lysate. The various oligomer conditions all contained SEQ ID NOs:12, 14, & 48 and also contained one of SEQ ID NOs:60, 18, 45, 46, 21, 3. The nucleotide sequences of the *Candida* oligos used in this Example are shown in Table 10 below.

TABLE 10

| SEQ ID NO: | Amplification Type | Sequence | Type |
|---|---|---|---|
| 12 | *Glabrata* | GCATTGGAGTTTCTGCTG | NT7 |
| 14 | *Glabrata* | AATTTAATACGACTCACTATAGGGAGAATACTGGACCGACATCCTTACG | T7 |
| 48 | *Glabrata* | GCTCAGAAAACCAGAAGCGAAACGGGTTTAAAAAAAAAAAAAAAAAAAAAAAAAAAAAAA | TCO |
| 60 | *Glabrata* (PR2) | GGAUGUGACUGUCAUGCCAUCC | torch |
| 18 | PR1 | GGUGGAUUUGUGCGACACCACC | torch |
| 45 | PR3 | CAUGCGCUUUUCUGAGAAGCAACGCAUG | torch |
| 46 | PR4 | CUGAGAAGCAACUUCUCUAUUAACGCUCAG | torch |
| 21 | PR5 | GGCAGAGACGUAUGGGCCUGCUGCC | torch |
| 3 | PR6 | CCAAGUCCUUGUGGCUUGGCCUUGG | torch |

Torch performance was evaluated by running RT-TMA amplification and detection reactions on 8 replicates of each of the targets per condition, with all reagents constant except for the identity of the torch probe. Reactions were done semi-manually, generally as described above, using a Torrey Pines heat block (Torrey Pines Scientific, CA, Cat. No. IC25), a Kingfisher® extraction system (ThermoScientific, MA, Cat. No. 5400500), a Thermomixer® (shaker/heat block) (Eppendorf, Hamburg DE, Eppendorf Model 5355) and a Stratagene® real time cycler (Model Mx3005p, Agilent Technologies, Santa Clara, CA) or a Panther system (Hologic, Inc., Marlborough, MA).

Results are shown in Table 11 below. Two of the six torch probes (PR4 and PR6) differentiated poorly between the no target control and *Candida glabrata* lysate target sample and were therefore unsuitable for use in the assay. Of the four remaining candidate torch probes, PR2 and PR1 had preferred performance compared to PR3 and PR5 due to lower Mean T-times and higher Mean T-slopes.

TABLE 11

| Torch ID | SEQ ID NO: | Mean T-time | Mean T-slope | Mean RFU Range | NTC RFU Range |
|---|---|---|---|---|---|
| PR1 | 18 | 12.20 | 0.1209 | 17229 | −243.1 |
| PR2 | 60 | 12.08 | 0.1139 | 19293 | −345.4 |
| PR3 | 45 | 13.35 | 0.0785 | 22770 | −790.4 |
| PR4 | 46 | 9.79 | 0.0751 | 16138 | 8001.6 |
| PR5 | 21 | 14.29 | 0.0687 | 21196 | −299.7 |
| PR6 | 3 | 6.3501 | 0.08585 | 3615 | 1486.8 |

Example 6: Alternate Non-T7 Primer Designs for Detection of *Candida* Species

Five individual non-T7 primers were tested using RT-TMA for the detection of the Broad Range *Candida* species. Each non-T7 primer was used at 15 pmol per reaction in the amplification mix. Common reagents were used for TCR and Promoter solutions. The TCR contained target capture oligos SEQ ID Nos:24 & 66 at 15 pmol/rxn each and T7 primer oligo SEQ ID NO:9 at 5 pmol/rxn. The promoter solution contained T7 primer SEQ ID NO:9 at 15 pmol/rxn and torch oligo SEQ ID NO:27 at 15 pmol/rxn. The non-T7 primers being compared are shown in Table 12 below.

TABLE 12

| Non-T7 Primers | |
|---|---|
| SEQ ID NO: | Sequence |
| 26 | CGTTACAAGAAATATACACGG |
| 34 | GGTAGTTTGGCTTTTCTTTGG |
| 73 | CTTCCTTAGCGTGAAAACGCA |
| 74 | AGGCTGTAAAAGGTCTGCTTCGT |
| 75 | AGAAATCTTCAGAGCCCGA |

The targets of the amplification were in vitro transcripts containing partial RNase PR1 gene sequences from each of the following species: *Candida albicans, Candida parapsilosis, Candida tropicalis*, and *Candida dubliniensis.*

Reactions were done semi-manually, using a Torrey Pines heat block, a Kingfisher® extraction system, a Thermomixer® (shaker/heat block) and a Stratagene® realtime cycler, and analyzed, as generally described in the above Example 5.

Results: the non-T7 primer SEQ ID NO:73 did not detectably amplify the targets. The non-T7 primer SEQ ID NO:74 amplified the targets with a faster T-time than did the non-T7 primer SEQ ID NO:26, while the non-T7 primer SEQ ID NO:75 amplified *C. parapsilosis* with a slower T-time than the non-T7 primer SEQ ID NO:34.

Example 7: Comparison of *Candida* Species Torches with Alternate Stem Configurations Two alternate torch designs were functionally compared to assess the potential impact of the design difference to clinical accuracy and analytical performance. The torches were designed to contain the same analyte specific region (for detection of Broad Range target nucleic acids (*C. albicans, C. dubliniensis, C. parapsilosis*, or *C. tropicalis*)), and the same linkers, but were varied in the 3'-most two bases. Both oligonucleotides were comprised of methoxy-RNA, with the two 3'-most bases either CC or GG.

Two experiments were conducted. In the first experiment, a multiplex *Candida* formulation was built (Broad Range oligos, *C. glabrata* oligos, and internal control oligos), but omitting the Broad Range torch oligo. The reagent was then split between two portions and either SEQ ID NO:27 or SEQ ID NO:155 was added at 15 picomole per reaction to complete each formulation. Each completed formulation was run on the Panther system against analytical (control) samples and pooled negative samples (residual vaginal swab material from presumed negative samples, pooled together then divided for equal testing with the two formulations). Data represent two pooled negative samples at 10 replicates per formulation per pool, and a positive control *Candida albicans* lysate at 1E4 colony forming units per milliliter at 5 replicates per formulation. As shown in Table 13 below, torch SEQ ID NO:155 gave higher positive control background-subtracted RFU ranges than did torch SEQ ID NO:27, with similar variability from replicate to replicate (% CV). Average background signal for these reactions was 3337 RFU for torch SEQ ID NO:27 and 1182 for torch SEQ ID NO:155. On pooled negative samples, torch SEQ ID NO:155 gave lower RFU ranges and lower variability from replicate to replicate (% CV) than torch SEQ ID NO:27. Based on these data, torch SEQ ID NO:155 provided better discrimination between positive and negative samples.

TABLE 13

RFU Ranges with two alternate torches

| torch | SEQ ID NO: 27 | SEQ ID NO: 155 | SEQ ID NO: 27 | SEQ ID NO: 155 | SEQ ID NO: 27 | SEQ ID NO: 155 |
|---|---|---|---|---|---|---|
| sample | *C. albicans* | *C. albicans* | pool 1 | pool 1 | pool 2 | pool 2 |
| min | 9342 | 22529 | 1950 | −574 | 461 | −612 |
| max | 10595 | 25923 | 3155 | −369 | 2427 | −456 |
| mean | 9972 | 24408 | 2498 | −486 | 1674 | −534 |
| stdev | 528 | 1497 | 428 | 61 | 593 | 56 |
| % CV | 5% | 6% | 17% | −13% | 35% | −10% |

In a second experiment, fifty clinical samples were run on an automated Panther system (Hologic, Inc., Marlborough, MA) with two formulations of *Candida* reagents (Broad Range reporting to FAM and *Candida glabrata* reporting to HEX). Formulation 1 used SEQ ID NO:27 (FAM torch) at 32 picomole per reaction, and Formulation 2 used SEQ ID NO:155 (FAM torch) at 10 picomole per reaction. The formulations were otherwise the same. The *Candida glabrata* (HEX) torch (SEQ ID NO:60) was present at 26 picomole per reaction in both formulations. Each clinical sample was run at 1 replicate with each formulation. Whereas the background signals were similar on the HEX channel for both formulations, formulation 1 had substantially higher background than formulation 2. Average background signals were 5645 (FAM-Formulation 1), 638 (FAM-Formulation 2), 1457 (HEX-Formulation 1), 1347 (HEX-Formulation 2). The distribution of background-subtracted RFU ranges from the 48 valid results is shown in Table 14 below (N=number positive out of 48 for each condition). For the HEX results, no samples gave RFU ranges between 1250 and 5000 RFU, allowing room for setting an RFU range threshold to discriminate between positive and negative samples. On FAM, formulation 2 also had strong separation between samples giving high or low RFU ranges, whereas formulation 1 did not. The absence of intermediate RFU range sample results in this experiment suggests torch SEQ ID NO:155 is a better performing torch than is SEQ ID NO:27 for the Broad Range oligo combination.

TABLE 14

Distribution of RFU Range Values for 48 samples

| RFU range | N (FAM) SEQ ID NO: 27 | N (FAM) SEQ ID NO: 155 | N (HEX) SEQ ID NO: 27 | N (HEX) SEQ ID NO: 155 |
|---|---|---|---|---|
| >10000 | 27 | 11 | 4 | 3 |
| 5000 to 10000 | 4 | 14 | 0 | 1 |
| 2500 to 5000 | 7 | 0 | 0 | 0 |
| 1250 to 2500 | 4 | 0 | 0 | 0 |
| 500 to 1250 | 3 | 0 | 2 | 0 |
| <500 | 3 | 23 | 42 | 44 |

SEQUENCES

TABLE 15

Exemplary Oligomer Sequences, Reference Sequences, and Regions

| SEQ ID NO | Sequence | Description |
|---|---|---|
| 3 | CCAAGUCCUUGUGGCUUGGCCUUGG | *C. glabrata* Detection Probe |
| 9 | AATTTAATACGACTCACTATAGGGAGATCAAGTTCGCATATTGCAC | *C. albicans* T7 Primer |
| 11 | AGTGCATTGGAGTTTCTGC | *C. glabrata* Non-T7 Primer |
| 12 | GCATTGGAGTTTCTGCTG | *C. glabrata* Non-T7 Primer |
| 13 | AATTTAATACGACTCACTATAGGGAGAACCGACATCCTTACGTAG | *C. glabrata* T7 Primer |
| 14 | AATTTAATACGACTCACTATAGGGAGAATACTGGACCGACATCCTTACG | *C. glabrata* T7 Primer |
| 18 | GGUGGAUUUGUGCGACACCACC | *C. glabrata* Detection Probe |
| 19 | AUGGGAAUGGCGCCGUGGAUGGCCCAU | *C. albicans* Detection Probe |

TABLE 15-continued

Exemplary Oligomer Sequences, Reference Sequences, and Regions

| SEQ ID NO | Sequence | Description |
|---|---|---|
| 21 | GGCAGAGACGUAUGGGCCUGCUGCC | *C. glabrata* Detection Probe |
| 23 | TCGGTATCGGGTGCTTGAATTTAAAAAAAAAAAAAAAAAAAAAAAAAAAAA | *C. albicans* Target Capture oligomer |
| 24 | AGATCGGTATCGGGTGCTTGTTTAAAAAAAAAAAAAAAAAAAAAAAAAAAAA | *C. albicans* Target Capture oligomer |
| 26 | CGTTACAAGAAATATACACGG | *C. albicans* Non-T7 Primer |
| 27 | GGAAUGGCGCCGUGGAUGGUUGCAUUGG | *C. albicans* Detection Probe |
| 28 | GCCGUCAGCCAACCAUCCACGGC | *C. albicans* Detection Probe |
| 31 | GGCGTTACAAGAAATAT | *C. albicans* Non-T7 Primer |
| 32 | GCGGCGTTACAAGAAATAT | *C. albicans* Non-T7 Primer |
| 34 | GGTAGTTTGGCTTTTCTTTGG | *C. parapsilosis* Non-T7 Primer |
| 36 | GGATGGAGCGTACCACCGAATTTCCTTTAAAAAAAAAAAAAAAAAAAAAAAAAAAAAA | *C. albicans* Target Capture oligomer |
| 37 | TACCACCGAATTTCCCACCCTTTAAAAAAAAAAAAAAAAAAAAAAAAAAAAAA | *C. albicans* Target Capture oligomer |
| 45 | CAUGCGCUUUUCUGAGAAGCAACGCAUG | *C. glabrata* Detection Probe |
| 46 | CUGAGAAGCAACUUCUCUAUUAACGCUCAG | *C. glabrata* Detection Probe |
| 48 | GCTCAGAAAACCAGAAGCGAAACGGGTTTAAAAAAAAAAAAAAAAAAAAAAAAAAAAAA | *C. glabrata* Target Capture oligomer |
| 60 | GGAUGUGACUGUCAUGCCAUCC | *C. glabrata* Detection Probe |
| 64 | GAAUGGCGCCGUGGAUGGUUGCAUUC | *C. albicans* Detection Probe |
| 65 | AGAUCGGUAUCGGGUGCUUGTTTAAAAAAAAAAAAAAAAAAAAAAAAAAAAA | *C. albicans* Target Capture oligomer |
| 66 | GATGGAGCGTACCACCGTTTAAAAAAAAAAAAAAAAAAAAAAAAAAAAAA | *C. albicans* Target Capture oligomer |
| 67 | CGGTATCGGGTGCTTGTTTAAAAAAAAAAAAAAAAAAAAAAAAAAAAAA | *C. albicans* Target Capture oligomer |
| 69 | CCAGAAGCGAAACGGGTTTAAAAAAAAAAAAAAAAAAAAAAAAAAAAAA | *C. glabrata* Target Capture oligomer |
| 72 | GCTGTAAAAGGCTTACTTCG | *C. albicans* Non-T7 Primer |
| 73 | CTTCCTTAGCGTGAAAACGCA | *C. albicans* Non-T7 Primer |
| 74 | AGGCTGTAAAAGGTCTGCTTCGT | *C. albicans* Non-T7 Primer |
| 75 | AGAAATCTTCAGAGCCCGA | *C. parapsilosis* Non-T7 Primer |
| 77 | TCAAGTTCGCATATTGCAC | THS of SEQ ID NO: 9 |
| 79 | ACCGACATCCTTACGTAG | THS of SEQ ID NO: 13 |
| 80 | ATACTGGACCGACATCCTTACG | THS of SEQ ID NO: 14 |
| 84 | AGATCGGTATCGGGTGCTTG | THS of SEQ ID NO: 24 |
| 87 | GCTCAGAAAACCAGAAGCGAAACGGG | THS of SEQ ID NO: 48 |
| 89 | AGAUCGGUAUCGGGUGCUUG | THS of SEQ ID NO: 65 |
| 90 | GATGGAGCGTACCACCG | THS of SEQ ID NO: 66 |
| 91 | CGGTATCGGGTGCTTG | THS of SEQ ID NO: 67 |
| 93 | CCAGAAGCGAAACGGG | THS of SEQ ID NO: 69 |

TABLE 15-continued

Exemplary Oligomer Sequences, Reference Sequences, and Regions

| SEQ ID NO | Sequence | Description |
|---|---|---|
| 98 | TCGGTATCGGGTGCTTGAA | THS of SEQ ID NO: 23 |
| 99 | GGATGGAGCGTACCACCGAATTTCC | THS of SEQ ID NO: 36 |
| 100 | TACCACCGAATTTCCCACCC | THS of SEQ ID NO: 37 |
| 102 | CCAAGUCCUUGUGGCUUGGC | THS of SEQ ID NO: 3 |
| 106 | GGUGGAUUUGUGCGACA | THS of SEQ ID NO: 18 |
| 107 | AUGGGAAUGGCGCCGUGGAUGG | THS of SEQ ID NO: 19 |
| 108 | GGCAGAGACGUAUGGGCCUG | THS of SEQ ID NO: 21 |
| 109 | GGAAUGGCGCCGUGGAUGGUUG | THS of SEQ ID NO: 27 |
| 110 | CAGCCAACCAUCCACGGC | THS of SEQ ID NO: 28 |
| 113 | CAUGCGCUUUUCUGAGAAGCAAC | THS of SEQ ID NO: 45 |
| 114 | CUGAGAAGCAACUUCUCUAUUAACG | THS of SEQ ID NO: 46 |
| 124 | GGAUGUGACUGUCAUGC | THS of SEQ ID NO: 60 |
| 128 | GAAUGGCGCCGUGGAUGGUUG | THS of SEQ ID NO: 64 |
| 129 | Accession No. DQ660433 (see FIG. 1) | *C. albicans* reference sequence |
| 130 | Accession No. DQ660436 (see FIG. 3) | *C. parapsilosis* reference sequence |
| 131 | Accession No. DQ660434 (see FIG. 2) | *C. glabrata* reference sequence |
| 132 | GCGGCGTTACAAGAAATATACACGG | *C. albicans* target hybridizing region |
| 133 | GTTACAAGAAATAT | *C. albicans* target hybridizing core sequence |
| 134 | ATACTGGACCGACATCCTTACGTAG | *C. glabrata* target hybridizing region |
| 135 | ACCGACATCCTTACG | *C. glabrata* target hybridizing core sequence |
| 136 | AGTGCATTGGAGTTTCTGCTG | *C. glabrata* target hybridizing region |
| 137 | GCATTGGAGTTTCTGC | *C. glabrata* target hybridizing core sequence |
| 138 | AGATCGGTATCGGGTGCTTGAA | *C. albicans* target hybridizing region |
| 139 | CGGTATCGGGTGCTTG | *C. albicans* target hybridizing core sequence |
| 140 | GGATGGAGCGTACCACCGAATTTCCCACCC | *C. albicans* target hybridizing region |
| 141 | TACCACCG | *C. albicans* target hybridizing core sequence |
| 142 | GGAAATATATCTTCCTGCTCAGAAAACCAGAAGCGAAACGGG | *C. glabrata* target hybridizing region |
| 143 | CCAGAAGCGAAACGGG | *C. glabrata* target hybridizing core sequence |
| 144 | GCTCAG | *C. glabrata* target hybridizing core sequence |
| 145 | AUGGGAAUGGCGCCGUGGAUGGUUGGCUG | *C. albicans* target hybridizing region |
| 146 | GCCGUGGAUGGUUG | *C. albicans* target hybridizing core sequence |
| 147 | GGAUGUGACUGUCAUGCGCUUUUCUGAGAAGCAAC | *C. glabrata* target hybridizing region |
| 148 | CAUGC | *C. glabrata* target hybridizing core sequence |

TABLE 15-continued

| SEQ ID NO | Sequence | Description |
|---|---|---|
| 149 | GCCGUGGAUGGUUGGCUGACGGC | *C. albicans* Detection Probe |
| 150 | GCCGUGGAUGGUUGGCUG | THS of SEQ ID NO: 149 |
| 151 | GCTGTAAAAGGYYTRCTTCG | *C. albicans* target hybridizing core sequence |
| 152 | AGGCTGTAAAAGGYYTRCTTCGT | *C. albicans* target hybridizing region |
| 153 | GTGAAAGCGCATGGGC | *C. albicans* non-T7 primer |
| 154 | GAAATCTTCAGAGCCCGAAGG | *C. albicans* non-T7 primer |
| 155 | GGAAUGGCGCCGUGGAUGGUUGCAUUCC | *C. albicans* Detection Probe |

(Table title: Exemplary Oligomer Sequences, Reference Sequences, and Regions)

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A detection probe for detecting a *Candida* (*C.*) *glabrata* target nucleic acid, said detection probe comprising (a) a *C. glabrata*-specific detection probe nucleotide sequence consisting of the sequence of SEQ ID NO:60, or the full complement thereof; and (b) at least one of (i) a label, wherein (A) the label is a fluorescent label and the detection probe further comprises a quencher, wherein the detection probe is a molecular torch or a molecular beacon, or (B) the label is a acridinium ester chemiluminescent label, (ii) a substitution at the 2' position of at least one ribose moiety, and (iii) a blocking group at or near the 3' end of the detection probe.

2. The detection probe of claim 1, wherein the detection probe comprises the label.

3. The detection probe of claim 2, wherein the label is the acridinium ester chemiluminescent label.

4. The detection probe of claim 2, wherein the detection probe comprises the fluorescent label and the quencher.

5. The detection probe of claim 4, wherein the detection probe is the molecular torch.

6. The detection probe of claim 4, wherein the detection probe is the molecular beacon.

7. The detection probe of claim 1, wherein the detection probe comprises the substitution at the 2' position of at least one ribose moiety.

8. The detection probe of claim 7, wherein the substitution at the 2' position of at least one ribose moiety is a 2' methoxy substitution.

9. The detection probe of claim 1, wherein the detection probe comprises the blocking group at or near the 3' end of the detection probe.

10. The detection probe of claim 9, wherein the blocking group is selected from the group consisting of an alkyl group, a non-nucleotide linker, an alkane-diol dideoxynucleotide residue, and cordycepin.

11. A kit comprising the detection probe of claim 1.

12. The kit of claim 11, further comprising at least one of (i) an amplification oligomer combination for amplification of a *C. glabrata* nucleic acid target region, wherein the detection probe is capable of binding to said target region; and (ii) a capture probe oligomer for purifying the *C. glabrata* target nucleic acid.

13. The kit of claim 11, further comprising a *Candida*-specific detection probe for detecting a *Candida* species (sp.) target nucleic acid from one or more of *C. albicans, C. parapsilosis, C. dubliniensis*, and *C. tropicalis.*

14. The kit of claim 13, further comprising at least one of (i) an amplification oligomer combination for amplification of a *Candida* sp. nucleic acid target region, wherein said target region is from one or more of *C. albicans, C. parapsilosis, C. dubliniensis*, and *C. tropicalis*, and wherein the *Candida*-specific detection probe is capable of binding to said target region; and (ii) a capture probe oligomer for purifying the *Candida* sp. target nucleic acid.

15. A reaction mixture comprising the detection probe of claim 1.

16. The reaction mixture of claim 15, further comprising at least one of (i) an amplification oligomer combination for amplification of a *C. glabrata* nucleic acid target region, wherein the detection probe is capable of binding to said target region; and (ii) a capture probe oligomer for purifying the *C. glabrata* target nucleic acid.

17. The reaction mixture of claim 15, further comprising a *Candida*-specific detection probe for detecting a *Candida* species (sp.) target nucleic acid from one or more of *C. albicans, C. parapsilosis, C. dubliniensis*, and *C. tropicalis.*

18. The reaction mixture of claim 17, further comprising at least one of (i) an amplification oligomer combination for amplification of a *Candida* sp. nucleic acid target region, wherein said target region is from one or more of *C. albicans, C. parapsilosis, C. dubliniensis*, and *C. tropicalis*, and wherein the *Candida*-specific detection probe is capable of binding to said target region; and (ii) a capture probe oligomer for purifying the *Candida* sp. target nucleic acid.

* * * * *